United States Patent [19]
Jeffries et al.

[11] Patent Number: 5,498,534
[45] Date of Patent: Mar. 12, 1996

[54] **METHOD OF REMOVING COLOR FROM WOOD PULP USING XYLANASE FROM *STREPTOMYCES ROSEISCLEROTICUS* NRRL B-11019**

[75] Inventors: Thomas W. Jeffries; Anthony C. Grabski, both of Madison, Wis.; Rajesh N. Patel, Louisville, Ky.; Graziano Elegir, Milan, Italy; George Szakacs, Dayka Gabor, Hungary

[73] Assignee: The United States of America as represented by the Secretary of Agriculture, Washington, D.C.

[21] Appl. No.: 453,289

[22] Filed: May 30, 1995

Related U.S. Application Data

[63] Continuation of Ser. No. 257,965, Jun. 8, 1994, abandoned, which is a continuation-in-part of Ser. No. 857,060, Mar. 25, 1992, Pat. No. 5,369,024.

[51] Int. Cl.$^6$ .................. D21C 3/00; C12N 9/24; C12N 1/20; C12P 19/14
[52] U.S. Cl. ............. 435/278; 435/200; 435/253.5; 435/886; 435/99
[58] Field of Search .................. 435/220, 253.5, 435/886, 278, 99

[56] References Cited

U.S. PATENT DOCUMENTS

| | | | |
|---|---|---|---|
| 4,514,497 | 4/1985 | Kit et al. | 435/235 |
| 4,687,741 | 8/1987 | Farrell et al. | 435/189 |
| 4,687,745 | 8/1987 | Farrell et al. | 435/278 |
| 4,690,895 | 9/1987 | Farrell | 435/278 |
| 4,692,413 | 9/1987 | Farrell | 435/278 |
| 4,711,850 | 12/1987 | Kit et al. | 435/235 |
| 4,725,544 | 2/1988 | Tan et al. | 435/200 |
| 4,753,884 | 6/1988 | Kit et al. | 435/235 |
| 4,950,597 | 8/1990 | Saxena et al. | 435/101 |
| 4,966,850 | 10/1990 | Yu et al. | 435/200 |
| 5,179,021 | 1/1993 | du Manoir et al. | 435/278 |
| 5,202,249 | 4/1993 | Kluepfel et al. | 435/201 |

FOREIGN PATENT DOCUMENTS

| | | |
|---|---|---|
| 0261080 | 3/1988 | European Pat. Off. . |
| 0345715 | 6/1989 | European Pat. Off. . |
| 0353342 | 2/1990 | European Pat. Off. . |
| 0383999 | 8/1990 | European Pat. Off. . |
| 0406617 | 1/1991 | European Pat. Off. . |
| 0408803 | 1/1991 | European Pat. Off. . |
| 0418201 | 3/1991 | European Pat. Off. . |
| 2557894 | 1/1984 | France . |
| WO8908738 | 9/1989 | WIPO . |
| WO9102791 | 3/1991 | WIPO . |
| WO9102839 | 3/1991 | WIPO . |
| WO9102840 | 3/1991 | WIPO . |
| WO93/03155 | 2/1993 | WIPO . |

OTHER PUBLICATIONS

Grabski et al., Applied & Environmental Microbiol., Apr. 1991, 987–92.
Kluepfel et al., Industrial Microorganisms: Basic & Applied Molecular Genetics, Chapt, 18, 1993.
Senior et al., (7) Xylans & Xylanases, 1992, 555–558, From Prog. Biotechnol.
du Manoir et al., in Proceedings of Int. Blch. Conf. pp. 123–138 (1991).
Elegir, et al., Abstract from 6th European Congress on Biotech. 13–17 Jun. 93.
Elegir, et al., Applied and Environmental Microbiology vol. 60, No. 7, pp. 2609–2615 Jul. 1994.
Grabski, et al., Protein Expression and Purification 4:120–129 (1993).
Patel, et al., Appl. Microbiol. Biotechnol. 39:405–412 (1993).
Pedersen, et al., "Bleach Boosting of Kraft Pulp Using Alk. Hemicell." International Pulp Bleaching Conference, Stockholm, Sweden vol. 2, pp. 107–121, Jun. 11–14, 1991.
Skerker, et al., International Bleaching Conf., Assoc. Pulp & Paper Engineers, Jun. 11–14, 1991.

*Primary Examiner*—David M. Naff
*Assistant Examiner*—Michael V. Meller
*Attorney, Agent, or Firm*—Janet I. Stockhausen; M. Howard Silverstein; John D. Fado

[57] ABSTRACT

A method of removing color from wood pulp is disclosed. The method comprises the steps of preparing a wood pulp, treating the wood pulp with the xylanase wherein the xylanase is capable of releasing chromophores from the pulp and extracting the wood pulp to remove chromophores. Also disclosed are substantially purified preparations of xylanase enzymes from bacterial isolates. The xylanase is preferably isolated xyl 3 obtained from *Streptomyces roseiscleroticus* NRRL B-11019, wherein xyl 3 has a molecular weight of approximately 21 kD as determined by SDS-gel electrophoresis and a pH optima of pH 5.0–7.0.

6 Claims, 29 Drawing Sheets

```
            0         5        10        15        20        25        30
         -|---------|---------|---------|---------|---------|--------- xyl 3              A T T I T T N Q T G Y D G M Y Y S F W T D G X X S V
xyl 2      X T V V T T N Q T G T H E G Y     Y Y S F X T D A P N
xyl 4      A E S T L G A A A Q Q S G Y       Y F G T A I A A G L L
xyl 1      A E S T L G A A A A Q S G R       Y F G T A I A A G R L G xyl 3      X M T L N X G
xyl 2      D S T Y
```

METHOD OF REMOVING COLOR FROM WOOD PULP USING XYLANASE FROM *STREPTOMYCES ROSEISCLEROTICUS* NRRL B-11019

This is a continuation of application Ser. No. 08/257,965 filed Jun. 8, 1994 now abandoned, which is a continuation-in-part of application Ser. No. 07/857,060 filed Mar. 25, 1992, now U.S. Pat. No. 5,369,024.

FIELD OF THE INVENTION

This invention generally relates to the removal of color from kraft wood pulps. Specifically, the invention relates to the use of a xylanase capable of removing chromophores in processing kraft pulps.

BACKGROUND OF THE INVENTION

The cell wall of wood fiber consists of several layers composed primarily of cellulose, hemicellulose and lignin. Pulping is a procedure that disintegrates these fibers by mechanical and chemical means. Ultimately this pulp will be used for papermaking. The objective of pulping is to separate the cellulose fibers and remove as much lignin and hemicellulose as required by the end use but to preserve the fiber strength.

Kraft pulping is a specific pulping process that uses a wide variety of wood sources to produce quality pulps for the manufacture of particularly strong paper. Kraft pulping is a highly alkaline method of wood chip digestion characterized by the use of sodium hydroxide and sodium sulfide in the delignification phase. The kraft process is now the most widely used of all pulping processes. Kraft pulp is commonly used for the production of grocery bag stock and linerboard for corrugated containers and is also incorporated with other pulps into numerous grades of paper, particularly book papers, newsprint, high grade magazine paper, other printing papers, bond and writing papers.

Colored compounds ("chromophores") are created during the kraft cooking process. Chromophores are believed to be derived from either the lignin or hemicellulose components of the fiber, but the chemistry and origin of chromophores are not well characterized. The bulk of chromophores diffuse out of the pulp and are removed in the spent black liquors or in the washing stages of the kraft pulping. However, some chromophores remain in the pulp where they are either physically trapped within the fibers by precipitated xylan or are chemically bound to the hemicellulosic and cellulosic moieties.

Therefore, kraft pulp has a brown color which must be removed before the pulp can be incorporated into writing papers or printing stock. The bleaching process commonly uses elemental chlorine, chlorine dioxide, or hypochlorous acid in aqueous solution. Unfortunately, chlorination results in the formation of large quantities of chlorinated aromatic degradation products that are toxic and difficult to remove by conventional waste treatment. Moreover, the bleaching process damages the pulp fibers by reducing the degree of polymerization of the cellulose, and residual acid left in the paper causes slow degradation over time. Newer bleaching processes employ hydrogen peroxide or, less commonly, oxygen/alkali ($O_2$/NaOH), but the bleaching activity of these chemicals is not great enough, particularly for high-yield pulps.

Enzymes are now commonly used to aid the pulping process. In recent years, there have been several reports that xylanases, enzymes that convert xylan to constituent sugars, will improve fiber flexibility in chemical pulps (Mora, et al. 1986, *J. Wood Chem. Technol.*, 6:147–165; Noé, et al. 1986, *J. Wood Chem. Technol.*, 6:167–184). Xylanases are known to remove residual xylan in the production of dissolving pulps (Paice, et al. 1984, *J. Wood Chem. Technol.*, 4:187–198), and to enhance the bleaching of kraft pulps (Viikari, et al. pages 67–69, in: *Biotechnology in the Pulp and Paper Industry*, Stockholm, 1986; Viikari, et al., pages 151–154, in: *Fourth International Symposium on Wood and Pulping Chemistry*, Paris, 1987; Chauvet, et al., pages 325–327, in: *Fourth International Symposium on Wood and Pulping Chemistry*, Paris, 1987). Chauvet, et al., supra 1987, reported that treating kraft pulps with xylanases lowered the lignin content of the pulps and lowered the amount of chemicals necessary for achieving a given degree of brightness. The mechanical strength properties of the sheets were not severely affected. Viikari, et al., supra 1987, has reported reductions of 25–50% in the amount of chlorine dioxide required for bleaching following treatment of kraft pulps with specific xylanases.

Many different microbial xylanase preparations have been reported in the literature. Most are derived from various fungal sources; a few are from Streptomyces and yeasts. See published PCT applications WO 91/02840, WO 91/02839, U.S. Pat. No. 4,966,850 and published European application 0 383 999.

In general, the xylanases that are most useful for facilitating the bleaching of kraft pulps are preparations that are free of cellulase activity. Enzymes that are active at neutral or alkaline pH would also be useful because large pH shifts would not be necessary in order to change the pulp from its alkaline state following the cook. Successive enzyme and alkali extraction steps would then be feasible. Temperature stability is also desirable because higher temperatures speed up enzyme activity and facilitate diffusion of the chromophores out of the pulp. The enzymes should be resistant to inhibition by the kraft degradation products. Enzymes that are capable of penetrating the micropore structure of the fibers would be very useful, because they would have access to a larger fraction of the chromophores. An enzyme that will cleave specifically at or near xylan moieties that are crosslinked into chromophores would be particularly useful, because color removal would be maximized while minimizing yield loss. Other than the present invention, there are no xylanases known to remove chromophores from wood pulp.

SUMMARY OF THE INVENTION

The present invention is a method of removing chromophores from wood pulp. The method comprises the steps of first preparing a wood pulp, treating the wood pulp with xylanase (wherein the xylanase is capable of releasing chromophores from the pulp) and then extracting the pulp to remove chromophores. In a particularly preferred embodiment of the present invention, the wood pulp is a kraft pulp and the xylanase is obtained from *Streptomyces roseiscleroticus* (NRRL 18985) and is selected from the group consisting of xyl 1, xyl 2, xyl 3, and xyl 4. In another preferred embodiment, the xylanase is a mixture of xylanases in a crude enzyme preparation from a culture of bacteria selected from the group consisting of Streptomyces sp. J2-5 (NRRL 18983), Streptomyces sp. TUB B-12-2 (NRRL 18982), and *Streptomyces thermonitrificans* TUB B-236 (NRRL 18984, ATCC 43908). In another preferred embodiment, the xylanase is a substantially purified preparation of a xylanase obtained from Streptomyces sp. TUB B-12-2 (NRRL 18982) where the xylanase is selected from the group consisting of xyl 1a, xyl 1b, xyl 2, xyl 3, and xyl 4. In another preferred embodiment of the present invention, the extraction is an alkali/hydrogen peroxide extraction.

The present invention is also a method of removing color from a wood pulp wherein the wood pulp contains secondary fiber. This method contains the steps of preparing a wood pulp, treating the wood pulp with xylanase (wherein the xylanase is capable of releasing chromophores from the pulp) and extracting the pulp to remove chromophores.

The present invention is also a method of removing chromophores from wood pulp containing the steps of preparing a wood pulp, treating the wood pulp with xylanase, wherein the xylanase is capable of releasing chromophores from the pulp. Chromophores are released from the pulp and the pulp is then extracted with an alkaline solution. The pulp is then subjected to bleaching. In particularly advantageous embodiments of the present invention the xylanase is selected from a group consisting of xyl 1, xyl 2, xyl 3, and xyl 4 from *Streptomyces roseiscleroticus* or from a group consisting of xyl 1a, xyl 1b, xyl 2, xyl 3, and xyl 4 from *Streptomyces sp.* TUB B-12-2, and the bleaching is oxygen bleaching.

The present invention is also a method of removing color from wood pulps. The method begins with the screening of xylanases to obtain a xylanase capable of releasing chromophores from wood pulp. Wood pulp is prepared and treated with the xylanase. The pulp is then extracted to remove the chromophores.

The object of the present invention is to remove color from wood pulps.

Another object of the present invention is to reduce the amount of bleaching necessary in the processing of wood pulps.

Another object of the present invention is to remove color from secondary fiber wood pulps.

An advantage of the present invention is that color may be removed from wood pulps without the use of bleach.

Another advantage of the invention is that the amount of chemical bleach used to remove color from a wood pulp may be reduced.

Other objects, advantages and features of the present invention will become apparent from the following specification when taken in conjunction with the accompanying drawings.

DESCRIPTION OF THE DRAWINGS

FIG. 6 is the N-terminal amino acid sequences of xyl 1, xyl 2, xyl 3 and xyl 4 from *S. roseiscleroticus*.

DESCRIPTION OF THE PREFERRED EMBODIMENT

A. In General

The present invention is a method of removing color from wood pulps. The method uses a xylanase capable of removing chromophores. We have isolated four xylanases from *S. roseiscleroticus* (NRRL 18985) and five xylanases from Streptomyces sp. TUB B-12-2 (NRRL 18982) that have different capabilities in releasing chromophores from kraft pulps. We have demonstrated that chromophore-removing xylanase activity is also present in Streptomyces sp. J2-5 (NRRL 18983), and *Streptomyces thermonitrificans* TUB B-236 (NRRL 18984, ATCC 43908). Other xylanases might be suitable.

All isolates were deposited on Jun. 29, 1992 at the Agricultural Research Culture Collection, Northern Regional Research Laboratory (NRRL), International Depositary Authority, 1815 N. University Avenue, Peoria, Ill. 61604, U.S.A. in accord with the terms of the Budapest Treaty, and have been demonstrated to be viable. The deposits will be maintained for at least 30 years or for five years after the last request for a sample. All restrictions on the availability to the public of these cultures will be irrevocably removed upon the maturation of this application into a patent.

The following section describes the xylanases from *S. roseiscleroticus* suitable for use in the present invention, xyl 1, xyl 2, xyl 3 and xyl 4. It further describes additional suitable xylanases from Streptomyces sp. TUB B-12-2. A preferred assay for the xylanases and chromophore removal and a preferred method of treating wood pulp with the enzymes is also described.

B. Characterization of the xylanases

We have isolated four endoxylanases from *Streptomyces roseiscleroticus*. These new xylanases are capable of diffusing into the micropore structure of the wood pulp where they bind to and hydrolyze the xylan, thereby releasing the colored materials and increasing the accessibility of the pulp to bleaching and extractive processes. The enzymes range in molecular weight from about 21 to 47 kDa, but they are capable of penetrating pores that are much smaller than indicated by their actual sizes. In addition, some of the xylanases appear to have a particular affinity for chromophores in the pulp. The *S. roseiscleroticus* xylanases can greatly reduce the chemical demand in chemical bleaching.

Four xylanases from *S. roseiscleroticus* have been purified to homogeneity. A preferential method for the purification of these xylanases is described in the Examples. The enzymes may be purified with other protein purification methods known in the art. Additionally, we envision that xylanases may be produced via a method in which genes encoding the enzyme are cloned and expressed in suitable hosts.

Figure 1:
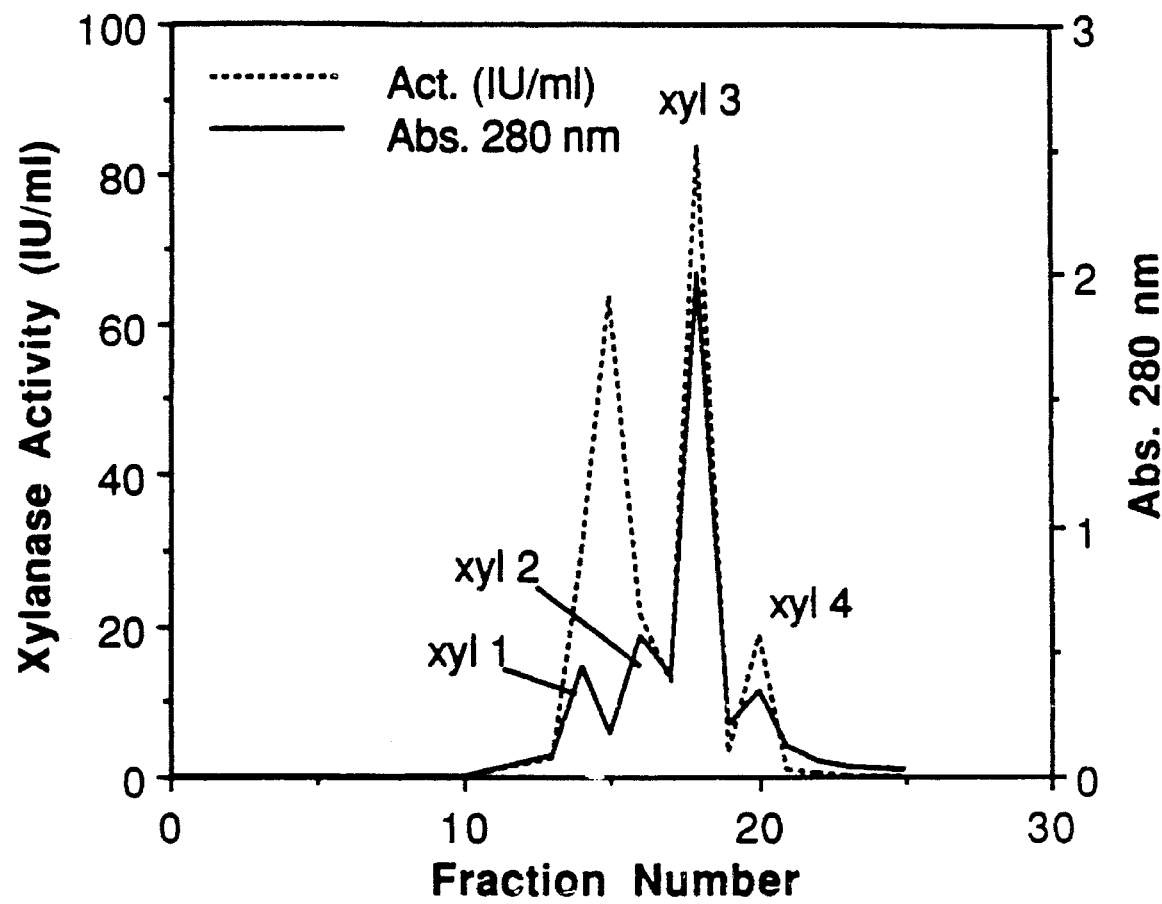
FIG. 1 is a chromatogram of both xylanase activity and absorbance at 280 nm of fractions from an SP 5PW column.
Figure 2:
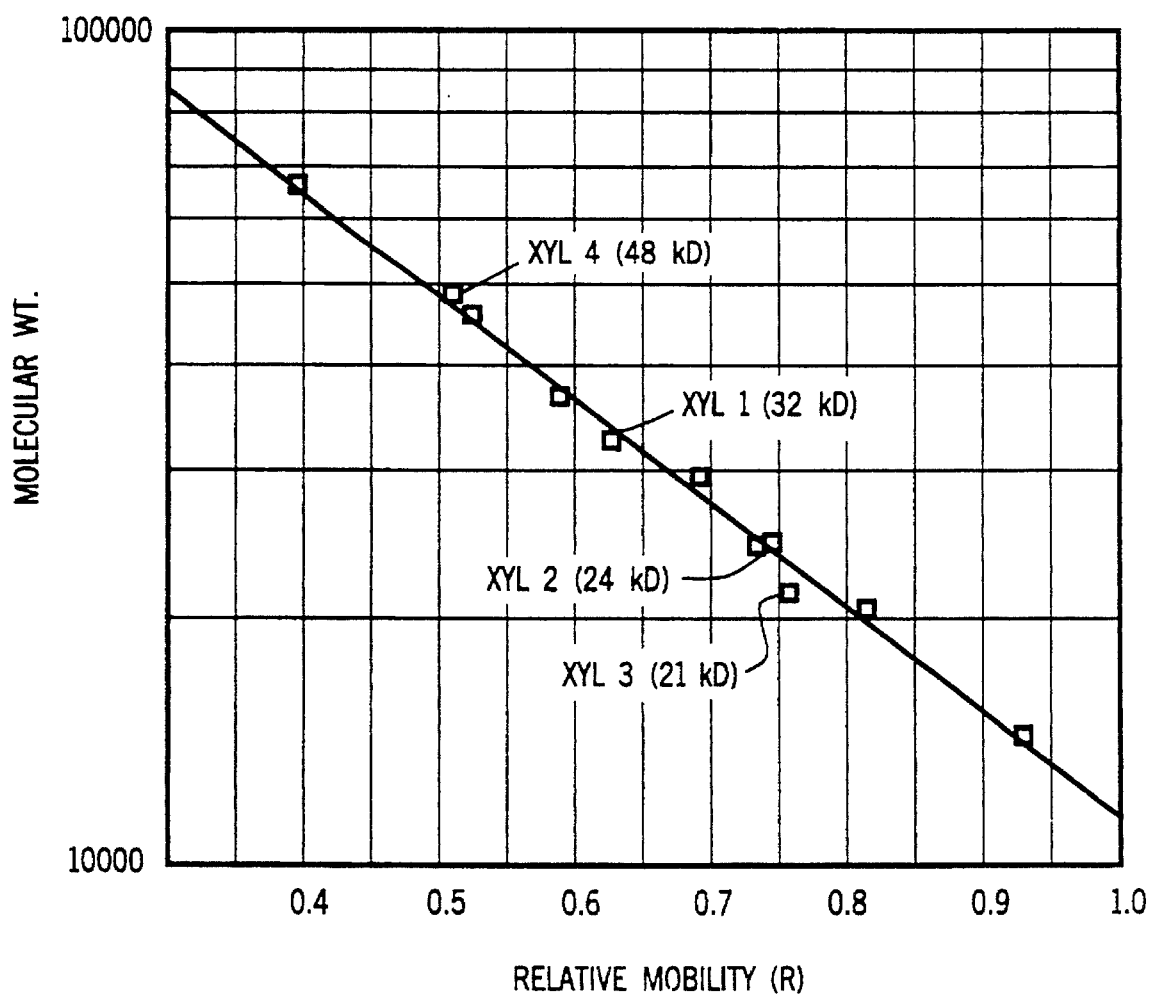
FIG. 2 is a diagram of molecular weight determination from an SDS gel electrophoretic analysis of the four xylanases.
Figure 3:
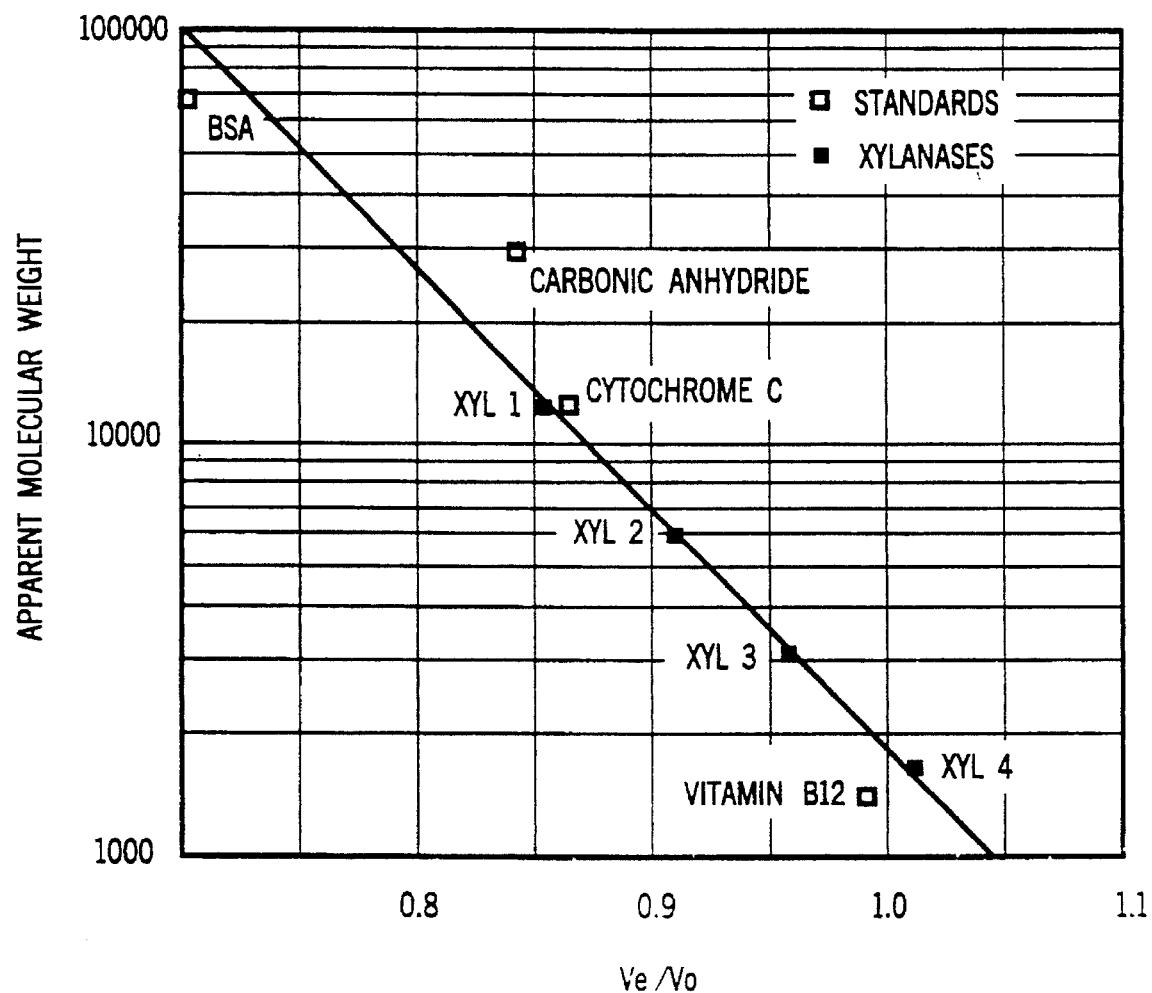
FIG. 3 is a molecular weight determination by native gel filtration on TSK.

We refer to these four isoenzymes as xyl 1, xyl 2, xyl 3 and xyl 4, according to their order of elution from a SP 5PW column (see FIG. 1). The molecular weights of the four xylanases have been estimated by both native gel exclusion chromatography using an HPLC/TSK column and by SDS (denaturing) gel electrophoresis. The apparent molecular weights determined by these two methods differ. The molecular weights estimated by denaturing gel electrophoresis, a method that is known to give a more accurate representation of true molecular weight of a protein, were between 21,000 Da and 42,000 Da (FIG. 2). By native size exclusion chromatography, the enzymes all appear to have very low molecular weights ranging from a little less than 2,000 to a little more than 10,000 Da. (FIG. 3). The molecular weight of all four xylanases have also been estimated by mass spectrometry, a method known to be extremely accurate, and found to be between 21,070 Da and 46,855 Da.

Figure 4:
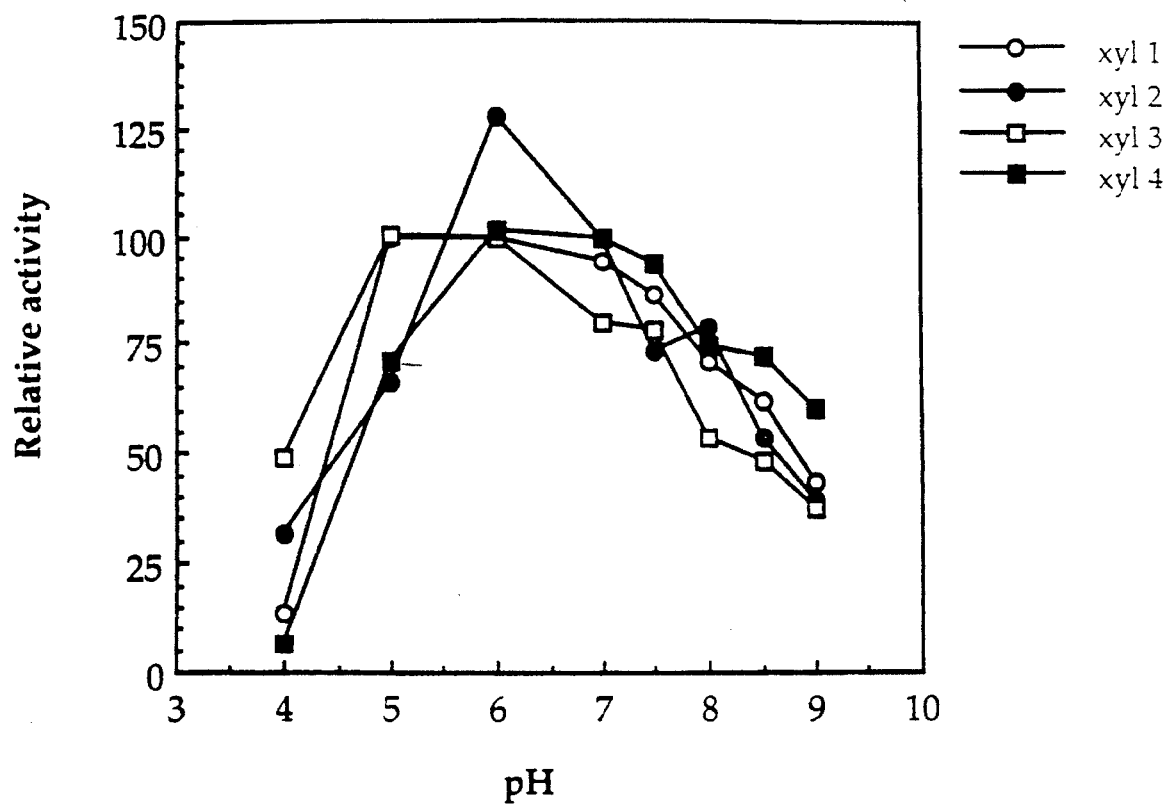
FIG. 4 is a graph of xylanase activity versus pH for four purified enzymes from *Streptomyces roseiscleroticus*.

The pH optima of the purified enzymes have been determined and found to lie in the range of 5 to 7, but a substantial amount of activity remains at pH 8 to 9 (FIG. 4). The pH optimum of the crude preparation is not significantly different, but the crude enzyme preparation is somewhat more stable. The pH range of 7 to 8 is appropriate for removal of chromophores from kraft pulps.

Figure 5A:
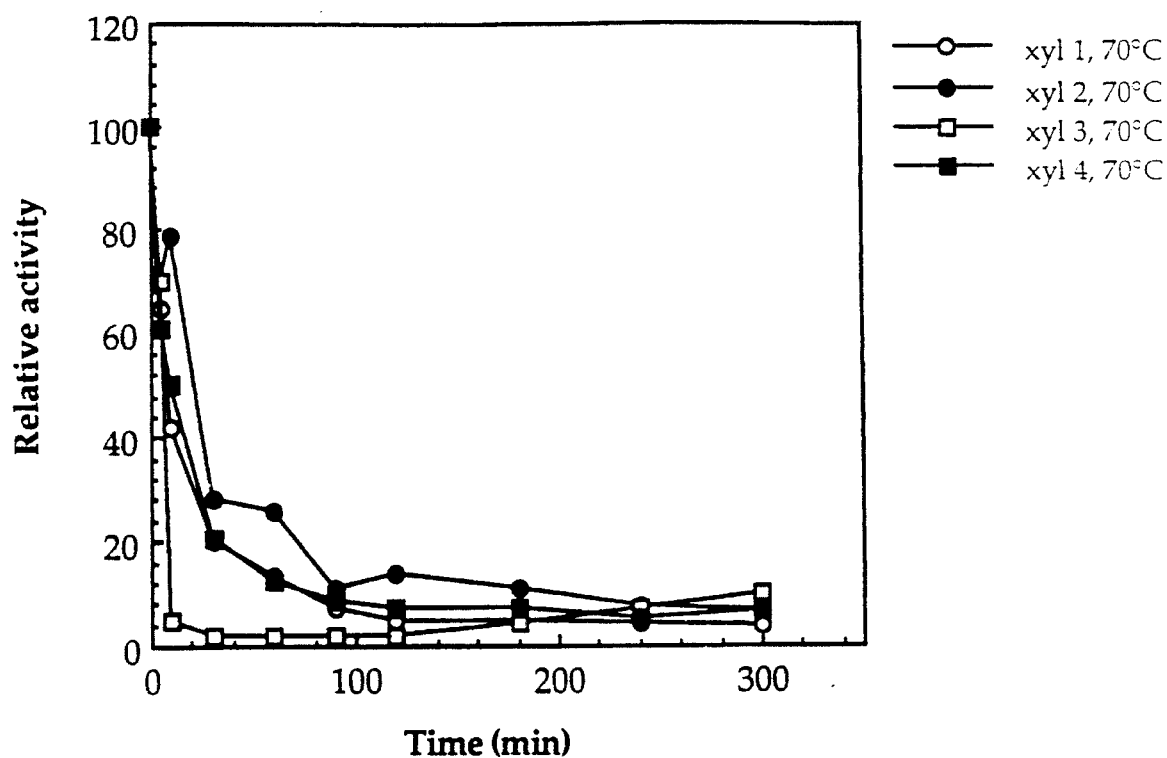
FIG. 5 is a graph of relative enzymatic activity versus time for the xylanases incubated at different temperatures.
Figure 5B:
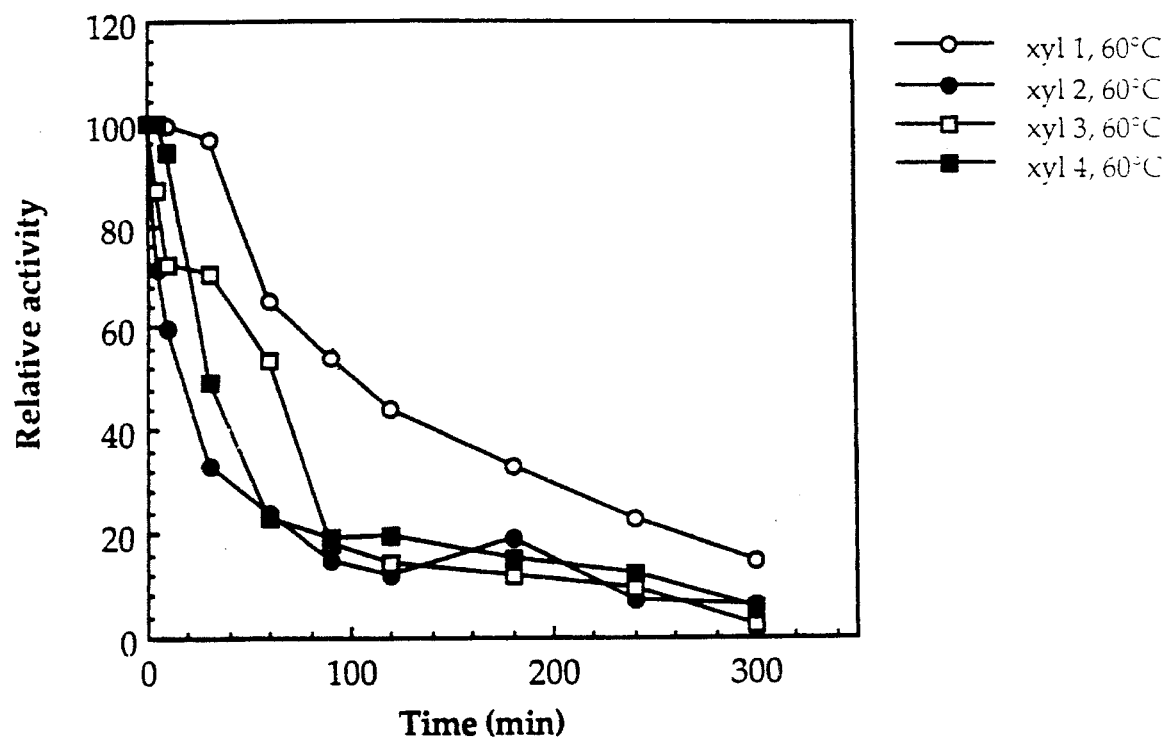
Figure 5C:
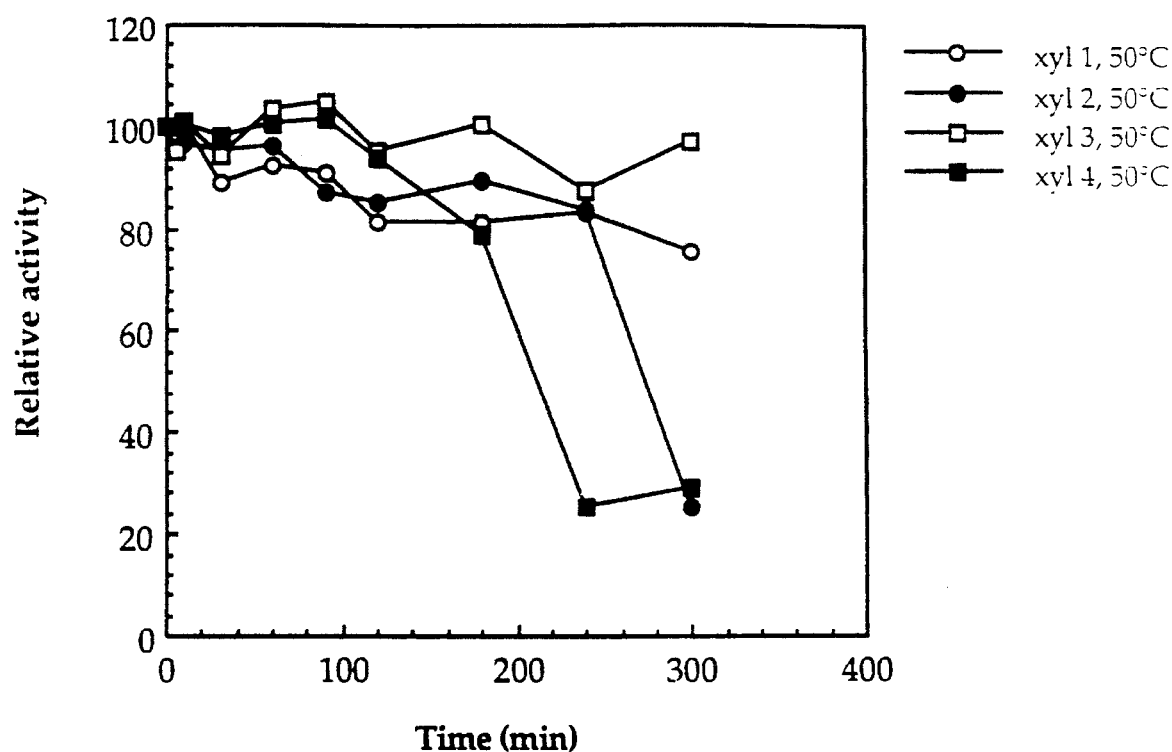

The thermal stability of the four xylanases have been determined at 50°, 60° and 70° C. At 70° C., activity is lost relatively readily, at 60° C., xyl 1 has a half-life of about 100 min; xyl 3 has a half-life of about 60 min (FIG. 5). Total xylanase activity is more stable in the crude (mixed) preparation.

All four of the xylanases exhibit an endo-action pattern, producing only xylo-oligosaccharides from oat spelts xylan. The smallest oligosaccharide observed is xylobiose. The enzymes appear to accumulate higher DP oligosaccharides (DP 10 to 18).

In comparison to many other microbial xylanases having pH optima in the range of pH 4.5 and temperature stabilities less than 40° C., the thermal stability (60° C.) and the activity of the *S. roseiscleroticus* xylanases at an alkaline pH (7 to 9) enable them to be used under conditions where the colored materials are more readily solubilized. Moreover, the relative specificity of the enzymes for chromophores minimizes pulp yield losses. Although our evidence does not indicate conclusively that the xylanases of *S. roseiscleroticus* are capable of cleaving bonds between carbohydrate and lignin or chromophores, the release of color from kraft pulp is consistent with this possibility.

We have further characterized the chromophore-removing xylanase activities in crude enzyme preparations of three additional bacterial strains, namely Streptomyces sp. J2-5 and sp. TUB B-12-2, and *Streptomyces thermonitrificans* TUB B-236. Five additional purified xylanase enzymes have been obtained from Streptomyces sp. TUB B-12-2 and have been designated xyl 1a, xyl 1b, xyl 2, xyl 3, and xyl 4.

The molecular weights of the five xylanases from B-12-2 have been estimated by SDS (denaturing) gel electrophoresis. The molecular weights estimated by denaturing gel electrophoresis, known to give a more accurate representation of true protein molecular weight, were between 23.8 kDa and 40.5 kDa.

The pH optima of the purified enzymes have been determined and found to lie in the range of 6 to 7, but a substantial amount of activity remains at pH 8 to 9. The pH optimum of the crude preparation is not significantly different, but the crude enzyme preparation is somewhat more stable. The pH range of 7 to 8 is appropriate for removal of chromophores from kraft pulps.

The temperature optima of the five B-12-2 xylanases have been determined to be 55° C. for xyl 1a and 60° C. for the four other xylanases. Total xylanase activity is more stable in the crude (mixed) preparation.

All five of the B-12-2 xylanases exhibit an endo-action pattern, producing only xylo-oligosaccharides from oat spelts xylan. The smallest oligosaccharide observed is xylobiose. The enzymes appear to accumulate higher DP oligosaccharides (DP 10 to 18).

In comparison to many other microbial xylanases having pH optima in the range of pH 4.5 and temperature stabilities less than 40° C., the thermal stability (60° C.) and the activity of the B-12-2 xylanases at an alkaline pH (7 to 8.5) enable them to be used under conditions where the colored materials are more readily solubilized. Moreover, the relative specificity of the enzymes for chromophores minimizes pulp yield losses. Although our evidence does not indicate conclusively that the xylanases of B-12-2 are capable of cleaving bonds between carbohydrate and lignin or chromophores, the release of color from kraft pulp is consistent with this possibility.

C. Enzyme Assay

A preferential method of xylanase assay is as follows: xylanase activity is determined as the μmoles of reducing groups produced from a model substrate (1% hot water soluble oat spelts xylan, Sigma) in a fixed amount of time (10 to 20 min) at a fixed temperature (60° C.) at a pH of 7.0 (50 mm phosphate buffer). Hot-water soluble oat spelts xylan (0.5 ml, 2%) is placed in a series of test tubes and equilibrated in a water bath. Serial two-fold dilutions of the enzyme are made in buffer, and 0.5 ml of each dilution is added to the substrate. The reaction is stopped by the addition of Nelson-Somogyi reagent C. (Somogyi, *J. Biol. Chem.* 195: 19–23, 1952). The mixture is boiled for 20 minutes, and cooled in a cold water bath. Nelson-Somogyi reagent D (1.0 ml) is added to each tube, mixed and 5 ml of water is added.

The absorbance of the solution is determined at 520 nm, and the μmoles of reducing sugars formed are compared to a standard of 0 to 300 μg of xylose. Suitable controls for the assay are the enzyme alone, substrate alone, and a buffer blank. Absorbances are determined against the buffer blank, and enzyme activities are corrected appropriately for background reducing activities. Because reaction rates are often substrate-limited, the reducing sugars observed in the two or three dilutions giving the highest consistent apparent enzyme activities are averaged. One International Unit (IU) of xylanase is defined as that amount of enzyme producing 1 μmole of reducing sugar equivalent (as xylose) in one minute under the conditions described.

D. Use of xylanases in pulping

Kraft bleaching is described in Fengel et al. *Wood: Chemistry, Ultrastructure, Reactions.* Walter de Gruyter, New York, 1984., pp. 463–473. In general, kraft bleaching comprises the following steps:

Pulp from the kraft digester is screened to remove knots, washed to remove black liquor, then screened, cleaned and thickened prior to being transferred to the brown stock holding tank or pulp chest. The pulp chest serves both as a surge tank to even out the flow of pulp from the digesters and as a mixing tank to blend the different batches of pulp. The residence time of the brown stock holding tank or pulp chest can vary from 30 minutes to 3 hours or more, depending on the timing of mill operations. Chromophore removal is usually carried out in multistage procedures with oxidative processes followed by alkaline extraction.

From the holding tank, the pulp passes to the bleach plant. In the first stage of bleaching, the pulp is adjusted to pH 2 either with HCl or by the addition of chlorine gas. (Note: some pH adjustment might be needed if the pulp is not fully washed or if chlorination is preceded by a strong alkali treatment). Chlorine gas dissolved in water is added with mixing.

The dose of chlorine employed depends upon the kappa number of the pulp. Kappa is determined analytically by measuring the amount of a potassium permanganate consumed by the pulp under defined conditions as given in TAPPI Standard Method 236 CM 85. Kappa number is the volume in milliliters of 0.1 normal potassium permanganate solution consumed by 1 g of OD (oven dry) pulp. The amount of chlorine added (given as % $Cl_2$ by weight based on the amount of pulp, i.e. grams chlorine/100 grams of oven dry pulp) is generally equal to 0.45×kappa. Generally one-half of the total chlorine demand is added in the first charge. The chlorine reacts with the pulp for 60 minutes at room temperature or 20 minutes at 40° C.

Following chlorination, the pulp is extracted with NaOH. The amount of NaOH employed, likewise depends on the kappa number, but generally the amount used is 0.6×the % $Cl_2$ used in the first chlorination stage. Subsequent oxidation stages can employ a mixture of $Cl_2$ and $ClO_2$ (chlorine dioxide) or simply chlorine dioxide in later stages. Generally, a 5–10% substitution of $ClO_2$ for $Cl_2$ is used but higher substitutions of $ClO_2$ have been employed to reduce the formation of chlorinated aromatics. (Note: the concentration of chlorine dioxide solutions is determined by titrating the amount of active chlorine present, so direct substitution of $ClO_2$ for $Cl_2$ is possible.) The amount of chlorine dioxide or the degree of substitution needs to be determined for the pulp employed.

A preferable method of treating a wood pulp with a xylanase capable of releasing chromophores is as follows: Xylanase is applied to the pulp after it emerges from the stock washers but before the pulp enters the bleaching process. The pulp consistency at the time of enzyme application can range from 6% to 18%. The preferable range is 8% to 12%. The pH of the pulp at the time of enzyme application can range from 4.5 to 9, but the preferable range is pH 7 to pH 8.5. The incubation temperature can range from 30° C. to 70° C., but is preferably in the range of 50° C. to 60° C. The amount of enzyme applied to the pulp can range from 0.05 to 5.0 units (U) per oven dry gram of pulp, but preferably is in the range of 1 to 3 U/g.

The enzyme is applied to the pulp in a dilute solution with good mixing of the pulp stock. Mixing is especially important for effective treatment at low dosing levels. The enzyme/pulp mixture is held for 0.5 to 3 h, but preferably for 1 to 2 h, during which time enzyme action takes place and chromophores are released. Following enzyme treatment, the pulp is filtered and washed to remove these chromophores and residual enzyme. If desired, the enzyme-treated pulp can be extracted with alkali or alkali plus hydrogen peroxide in order to remove lignin prior to the bleaching stage. The enzyme-treated pulp is then bleached following any one of several bleach processes or sequences.

E. Assay for release of chromophores

Release of chromophores is routinely assayed by measuring the optical density of the supernatant solutions after enzyme treatment (stage 1) or alkali extraction (stage 2). Complete spectra may be obtained from 200 to 400 nm, or the absorption may be measured at 237 nm. Absorption in the visible region (400 to 700 nm) is usually minimal and results in a flat spectrum. Alkali-extracted materials often absorb strongly in the region between 260 and 280 nm.

F. Other xylanases capable of releasing chromophores

The exact number of species that produce xylanases is not known. Xylanases are commonly made by fungi, Bacillus, Streptomyces, and by other Actinomycetales. To obtain other xylanases capable of releasing chromophores, one would first identify an organism capable of growing on xylan. Preferably it would grow at elevated temperatures (>50° C.) and at elevated pH (>9). Once isolated, the organism would be cultivated on appropriate media, and the xylanase activity would be measured. The ability of the enzyme preparation to release chromophores would be determined by incubating a crude or partially purified enzyme preparation with kraft pulp. The efficacy of chromophore release would be measured by determining the optical density of supernatant solution.

The xylanase may be a naturally occurring xylanase or may be obtained from a cloned gene. The enzyme would then be used to treat a wood pulp, preferably as described above. The pulp could then be analyzed, as described above, to determine whether chromophores had been released.

We have developed a systematic process for isolating and screening novel microbes for their abilities to release chromophores. The rationale for our isolation and screening process is the following: Organisms that are most useful would be expected to grow on the residual materials left after wood or pulp decay. Streptomyces, a genus known to produce xylanases, are normally soil-inhabiting organisms, and species capable of removing chromophores composed of lignin or hemicellulose degradation products should be found growing on extensively rotted wood or leaf litter.

Streptomyces are also known to grow favorably under neutral to alkaline conditions. Useful isolates could also be found in soils, mud or aqueous systems receiving or in the vicinity of facilities receiving effluent from kraft pulp or bleach plants.

One suitable method of obtaining novel isolates is the following: An extract or infusion of rotted pine, birch, compost or leaf litter is made by crumbling or shredding the material and placing it in a large beaker. The material is covered with water and allowed to simmer for 15 to 60 minutes. The liquid is removed by filtration through several layers of cheesecloth and sterilized by autoclaving. Rotted birch wood is preferred for its high hemicellulose content.

Approximately 300 ml of the infusion is diluted with 700 ml of water. 1.0 g of yeast extract is added along with 15 to 18 g of agar. Minerals, other trace elements and fungal inhibitors may be added if desired. (See Hunter-Cevera, J. C., et al. 1986. In: Demain, A. L. and Solomon, N. A. *Manual of Industrial Microbiology and Biotechnology*, American Society for Microbiology, Washington, DC). The agar is dissolved by heating, the solution is sterilized by autoclaving and poured into sterile Petri plates. After the agar solidifies, the plates are allowed to dry for several days at room temperature or for up to an hour in a sterile hood with a fan blowing and the lids cracked. Care is taken to periodically rotate the plates so that drying is even.

Soil, mud or water samples are gathered from various habitats. Neutral to alkaline soils are preferred, as are soils with high organic content. Samples may also be taken from compost piles, rotted wood, the surfaces of plants or from plant root rhizosphere. A plurality of samples are removed from multiple soil horizons or micro-habitats. The soil samples are either used fresh or are allowed to air dry, screened to remove large particles, and ground with a mortar and pestle. The soil may then be applied to the surface of the isolation agar either by using a moistened foam sponge or by dilution and plating. Foam sponges of the type used to seal culture tubes are very suitable. The sponge is dipped into the soil, the excess soil is removed by gentle tapping, then the sponge is repeatedly pressed against the surface of the agar in a progressive circular pattern. Up to 20 impressions may be made on a single standard Petri dish. Multiple types of agar may be employed in alternating sequence. In using the dilution and plating technique, 1 g of dried, pulverized soil is diluted in 100 ml of sterile 0.85% NaCl in a 500 ml Erlenmeyer flask, and shaken at 250 rpm for 15 to 30 min. Samples are removed and carried through a series of dilutions. Samples from each of the dilutions are then spread onto the surface of the agar with a bent glass rod.

Replicate plates are incubated at 30° C., 35° C., 40° C., and 55° C. and are periodically examined for microbial growth. Colonies exhibiting characteristic features of Bacillus or Actinomycetes are isolated by removing them from the plate with a sterile toothpick or a sterile needle and by streaking them for isolation on a fresh plate of the same medium from which they are isolated.

Secondary screening of the organisms consists of testing the ability of the isolate to grow on alkali-extracted, milled wood enzyme lignin (AEMWEL) as a sole carbon and energy source. AEMWEL is made by the following procedure: Pine or birch chips are soaked in 1% sodium hydroxide (oven dry wood basis) at 37° C. overnight. The alkali extract is removed by filtration; the wood chips are washed repeatedly by soaking in water and rinsing until the rinse water is less than pH 7.5. The chips are then dried and ground in a Wiley mill to pass a 40 mesh screen. The ground wood is then extracted with acetone:water (90:10). The extracted, ground wood is dried extensively in a vacuum oven to remove all residual moisture. Once dry, the wood is ball-milled for 48 h. The ball-milled wood is digested in several successive treatments with an excess mixture of cellulases and hemicellulases. Enzymes are removed by repeatedly washing the residual AEMWEL in distilled water and recovering the solids by centrifugation. The residual AEMWEL consists essentially of lignin covalently attached through alkali-stable bonds to residual carbohydrate moieties. Other methods for isolating lignin or lignin-carbohydrate compounds may be suitable. See Azuma, et al. *Methods Enzymol.* 161:12–18 (1988); Obst, et al. *Methods Enzymol.* 161:3–12 (1988).

AEMWEL is used as a sole carbon and energy source in the second round of screening. A low concentration (0.5%) of AEMWEL is suspended in distilled water plus trace elements and 0.1% to 0.55% yeast extract, 1.5 to 1.8% agar is added and dissolved and the solution is sterilized by autoclaving as previously. Small aliquots (1.0 ml each) are placed in each well of 24-well plates and allowed to solidify. Each isolate is inoculated into a single well of the plate, and the plates are incubated at a suitable temperature (30° to 45° C.). After 5 to 20 days, the plates are examined and the isolates are scored for growth. Isolates capable of growing on AEMWEL are subjected to a third screen consisting of an ability to produce clearing zones in agar plates containing 0.5 to 2% oat spelts xylan or glucomannan as the sole carbon and energy source.

Isolates showing relatively good growth on AEMWEL and large clearing zones on xylan or glucomannan are screened for their ability to release color from kraft pulp. In this screening procedure, isolates are cultivated as described for *Streptomyces roseiscleroticus*, and the supernatant solution is assayed for enzyme production. The obtained enzymes are assayed as above for their ability to release chromophores.

Isolates may also be obtained from culture collections and screened in this manner. Cultures may be grown under several different aeration rates, and the supernatant solutions are harvested and concentrated.

EXAMPLES

1. Preparation of *S. roseiscleroticus* cultures. *Streptomyces roseiscleroticus* (NRRL B-11019) was obtained from David P. Labeda, USDA Northern Regional Research Laboratory, Peoria, Ill. The strain may be obtained from the Northern Regional Research Center, Peoria, Ill. *S. roseiscleroticus* was cultured on a xylan medium (YMX=yeast extract, 4.0 g/l; malt extract, 10.0 g/l; xylose, 4.0 g/l; agar 15 g/l; pH was adjusted to pH 7.3 prior to autoclaving) in order to achieve maximum xylanase enzyme production. It was essential to subculture the organisms frequently (every two weeks) in order to maintain viability. Stock inocula were preserved at an early stage by cutting plugs of agar from one-week old YMX agar plates and freezing at −70° C. in 10% (v/v) sterile glycerol. In order to obtain maximal xylanase production, it was necessary to prime the cultures in TSB as described by Morosoli, et al., *Biochem. J.*, 239: 587–592 (1986).

Seven-day old (or sporulating) slants grown on DX agar were washed with sterile TSnB. 10 ml were used to inoculate 100 ml of TSB in a 500 ml Erlenmeyer flasks stoppered with cotton plugs. Cultures were incubated at 37° C. to 38° C. with shaking at 240 rpm for 24 hours. The full 110 ml inoculum was added to 500 ml of XP medium in a 2800 ml Fernbach flask (see Grabski and Jeffries, Appl. Environ. Microbiol. 57:987–992 (1991). Cultures were incubated at 37° C. to 38° C. with shaking at 240 rpm for 48 to 72 hours. Xylanase assays were performed at 12 to 24 hour intervals, and cultures were harvested when xylanase activity peaked. Duplicate cultures were used for xylanase production.

To assay for xylanase activity, samples (1.0 ml) were taken every 24 hours and cells were removed by centrifugation (10,000× g, 15 min.). All sugar analyses were performed by the Nelson-Somogyi method (*J. Biol. Chem.* 195: 19–23, 1952) using either D-xylose or D-glucose as a standard. The 1 ml samples were centrifuged at 10,000× g for 15 min. to pellet and remove the cells. Supernatant solutions were then decanted and assayed for xylanase activity. Xylanase assays employed 0.25 ml of 1% oats spelts xylan (Sigma) plus 0.25 ml of appropriately diluted enzyme in 50 mM sodium phosphate buffer, pH 7.0. Xylan was solubilized in 0.5 N NaOH and neutralized with 1.0N HCl. Reactions were started by the addition of substrate and incubated for 10 min at 60° C. Reactions were stopped by the addition of Nelson-Somogyi reagent C. Cultures were sampled and assayed on a daily or more frequent basis. Maximal titers of xylanase activity were generally attained on day 3 or 4. The optimal time of harvest could be determined experimentally by leaving one or more flasks on the shaker and continuing to sample them after the time of harvest.

Cellulase activity was assayed only at peak xylanase time points. Cellulase assays were performed in the same manner as above except that 1% carboxy methyl cellulose (CMC, low viscosity, Sigma) was used as a substrate, and the assay temperature was reduced to 55° C. The ratio of xylanase to cellulase activities in the crude preparation was generally greater than 75. In the purified xylanase preparations, cellulase activity was not detected.

2. Enzyme Purification.

Step (a) Clarification. Cells were harvested by centrifugation (10,000× g, 30 min). The dark red supernatant was decanted and cell pellets were discarded. The supernatant was treated with the minimum amount of Biocryl BPA-1000 (Rohm and Haas Co., Philadelphia, Pa) required to precipitate pigments to approximately 20% of the initial value, as measured by reduction in absorbance at 392 nm. BPA-1000 is used as supplied by the manufacturer and typically 1.5% to 2.5% (v/v) is required for clarification. After stirring with the BPA for 5 min. at 4° C., a milky-grey floc was formed. This precipitate was removed by centrifugation at 15,000× g for 15 minutes. The clear, light yellow supernatant that remained was filtered through Miracloth (Calbiochem, La Jolla, Calif.).

Step (b) Concentration. The BPA-clarified filtrate was concentrated 5-fold by ultrafiltration in a Lab 1 EX ultrafiltration system (Rohm and Haas Co., Philadelphia, PA) using a 0.093 $m^2$ PM-1 hollow-fiber cartridge (1,000 mol wt cut-off) at a transmembrane pressure of 10 psi. The retentate (200 ml) was diafiltered with 250 ml of 100 mM pH 5.5 sodium acetate buffer followed by 500 ml of 10 mM pH 5.5 sodium acetate (Buffer A). Final retentate volume after diafiltration was approximately 200 ml.

The retentate was transferred to a 50 ml stirred ultrafiltration cell (Amicon Div., Grace & Co., Danvers, Mass.) equipped with a YM-3 disc membrane (3,000 mol wt cut-off) and concentrated 5-fold. The retentate was diafiltered with buffer A until a pH of 5.5 was attained. The volume was approximately 40 ml after diafiltration.

Step (c) Purification. The YM-3 retentate was centrifuged at 15,000× g, 15 min. Pellets were discarded and the supernatant, 40–60 mg protein/load, was applied (6 ml/min.) to a 21.5 mm ×150 mm TSK SP-5PW column. Proteins were separated using a gradient HPLC system (Beckman Instruments, Inc., Waldwick, N.J.) consisting of two 114M preparative head pumps, model 165 variable wavelength detector, and model 210A sample injection valve. The elution buffers were buffer A and buffer A+1.0M NaCl (buffer B). Unbound proteins were washed from the column with 100% buffer A/15 min. Chromatography of adsorbed proteins was achieved with a discontinuous gradient of buffer A/B as follows [%(v/v) A/min.]: 100/0, 100/5, 50/30, 0/32, 0/35, 100/37, and 100/50. Elution was monitored by absorbance at 280 nm for protein, and 6-ml fractions were collected. A chromatogram describing this elution is presented at FIG. 1. The order of elution on the SP 5PW column determined our nomenclature for the four xylanases.

Fractions containing xylanase activity against oat spelt xylan, as measured above, were pooled according to activity, protein chromatogram, and SDS-PAGE determinations of purity. The four xylanase peaks containing the highest enzyme activity and absorbance at 280 nm eluted between 300 and 400 mM NaCl. Xylanase fractions from three HPLC runs were concentrated and diafiltered into buffer A to a final protein concentration of approximately 9 mg/ml, using a stirred ultra-filtration cell as described above. $(NH_4)_2SO_4$ was added to the sample to a final concentration of 1.25M. The sample was microfuged at 16,000× g for 3 min. Pellets were discarded and the supernatant, 20–30 mg protein/load, was applied (1 ml/min.) to a 7.5 mm×75 mm TSK Phenyl-5PW column. Proteins were separated using a Beckman gradient HPLC system consisting of a 126 dual analytical pump, a model 165 variable wavelength detector, an IBM PC based data/system controller (Beckman System Gold software), and a model 210A sample injection valve. Elution buffers were buffer A and buffer A +1.25M $(NH_4)_2SO_4$ (buffer C). Unbound proteins were washed from the column with 100% buffer C/10 min. Chromatography of adsorbed proteins was achieved with a discontinuous gradient of buffer C/A as follows [%(v/v) C/min.]: 100/0, 100/5, 35/8, 0/25.5, 0/30, 100/32, and 100/45. Elution was monitored at 280 nm for protein, and 1-ml fractions were collected. The *S. roseiscleroticus* xyl 3 peak is commonly homogeneous after this step. Xyl 1, xyl 2 and xyl 4 must be further purified by gel-filtration chromatography.

Fractions were pooled according to activity, protein chromatogram, and SDS-PAGE determinations of purity as above. Pooled fractions of xyl 1, xyl 2, xyl 3 and xyl 4 from the Phenyl-5PW HPLC runs were concentrated and diafiltered into 200 mM pH 7.0 sodium phosphate (Buffer D) to a final protein concentration of approximately 5–10 mg/ml, using a Centricon-3 (Amicon DiV., Grace & Co., Danvers, Mass). The enzyme was microfuged at 16,000× g for 3 min. Pellets were discarded and the supernatant, 200–600 µg protein/load, was applied (1 ml/min.) to a 7.8 mm×150 mm TSK QC-PAK gel-filtration column. Proteins were separated using the Beckman analytical HPLC system previously described using isocratic elution with buffer D. Elution was monitored at 280 nm for protein, and 0.5 ml fractions were collected. Purified xylanases (10 mg/ml) were stored in 50 mM sodium phosphate buffer pH 7.0 at 70° C.

Protein purity and molecular weight were determined by sodium dodecyl sulphate polyacrylamide gel electrophoresis (SDS PAGE) on a Pharmacia Phast System (Piscataway, N.J.) using 10% –15% gradient polyacrylamide gels and a Sigma SDS-7 standard (Sigma Chemical Co., St. Louis, Mo.) containing seven proteins in the 14,200 to 66,000 mol wt range, staining with Coomassie Brilliant Blue G250. FIG. 2 describes the results of this analysis. The four xylanases are 21–48 kDa.

Protein concentrations were determined by the method of Lowry et al. (1951), with bovine serum albumin, Cohn fraction V (Sigma Chemical Co. St. Louis, Mo.) as standard.

3. Enzyme characterization.

Protein purity and molecular weight were determined by gel-filtration chromatography using the same TSK QC-PAK column and conditions described above in the purification protocol. Sigma standards for gel-filtration and corresponding molecular weights were: blue dextran (2,000,000), bovine serum albumin (66,000), cytochrome C (12,400), and vitamin $B_{12}$ (1,400). The results are described in FIG. 3, where molecular weights range from 1,400 to 66,000 Da.

The molecular mass of all four xylanases was determined with a Finnigan MAT TSQ-700 triple sector quadrupole mass spectrometer equipped with an electrospray ion source. Samples were introduced with an on-line capillary HPLC. A standard water, acetonitrile, trifluoroacetic acid buffer system was used in the chromatography (Beavis, 1990 reference). Scans over the mass range m/z 500–2000 were taken at 5 sec. intervals during the course of the liquid chromatography run. Chromatograms were generated by monitoring the ion current to the mass spectrometer detector. Mass spectra were collected as centroid data.

The molecular weights of the four xylanases as determined by Mass spectrometry were as follows:

TABLE 1

| | |
|---|---|
| xyl 1 | 33,647 Da |
| xyl 2 | 33,655 Da |
| xyl 3 | 21,070 Da |
| xyl 4 | 46,855 Da |

Thus, even though xyl 1 and xyl 4 have similar N-terminal amino acid sequences, they can be distinguished by their molecular masses. Even though xyl 1 and xyl 2 have similar molecular masses, they can be distinguished by their amino acid sequences.

Figure 11:
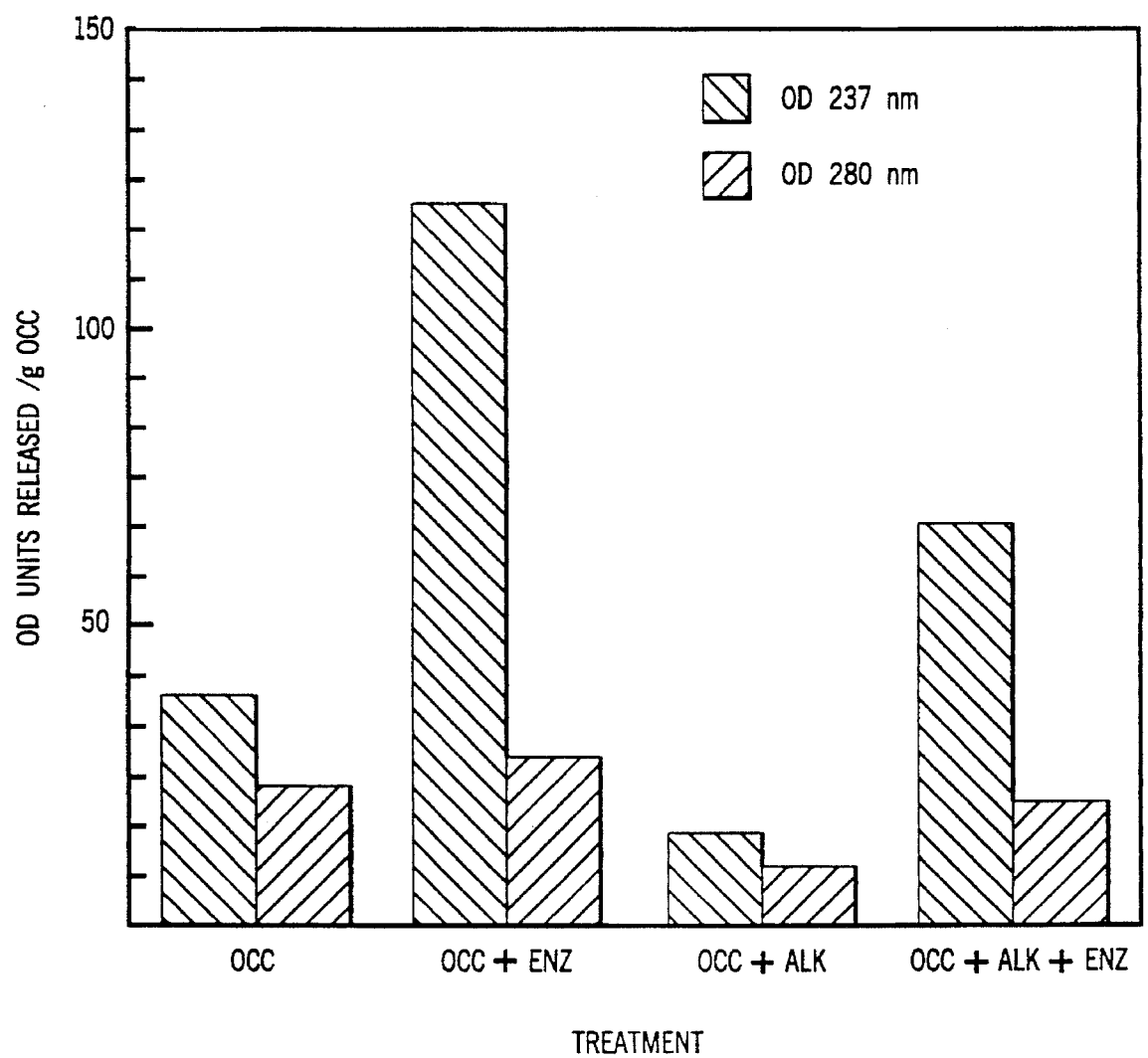
FIG. 11 is a diagram comparing release of chromophores versus different treatments involving old corrugated containers (secondary fibers).

N-terminal sequences were determined by gas phase sequencing on Applied Biosystems (Foster City, Calif.) model 475A protein sequencer at the University of Wisconsin Biotechnology Center using the protocols, reagents, and solvents supplied by the manufacturer. The N-terminal amino acid sequences of all four of the enzymes were determined and are described in FIG. 6 and at SEQ ID NOs: 1–4. Where the amino acid could not be identified, an X is shown. The sequences are lined up to maximize homology. Single letter designations stand for the various amino acids. Residues are boxed in FIG. 11 to indicate homology. Referring to FIG. 11, two of the xylanases (xyl 1 and xyl 4) had some similarity of their N-terminal amino acid sequences (88% homology). The other two xylanases (xyl 2 and xyl 3) showed about 37% homology. All four enzymes possess some common amino acid sequences.

With regard to N-terminal amino acid sequence, xyl 3 appears to be similar to other low molecular weight xylanases described from Streptomyces (published PCT application WO 91/02791; published European application 0 353 342). However, the molecular weight of xyl 3 differs from that reported for the xylanase described in 0 353 342 (5,000 Da) and WO 91/02791 (25,000 Da). Additionally, there are amino acid sequence differences between the xyl 3 sequence and the N-terminal amino acid sequences from the two reported xylanases. The amino acid sequences of xyl 1, xyl 2 and xyl 4 are novel.

4. Treatment of Pulp a. In General.

The clarified, concentrated, and diafiltered xylanase enzyme preparation was then diluted and applied to kraft pulp at the desired concentration. In general, the treated pulp is incubated with the enzyme, washed, extracted with NaOH, and bleached with an amount of bleach determined from the kappa of the enzyme-treated pulp. We found that the xylanase-treated pulp has a lower kappa and, therefore, requires less bleach than the control pulp in order to achieve the same brightness in both samples. The following examples illustrate the treatment of kraft pulps with the *S. roseiscleroticus* xylanases.

b. Kappa reduction of kraft pulp by *S. roseiscleroticus* xylanases.

The kraft pulp consisted of mixed northeastern U.S. hardwoods (chiefly aspen). The starting material consisted of 18.3% solids. The initial kappa number of the pulp was 16.3. 150 g OD was thoroughly washed prior to use. The starting pH was 7.8, and the final wet wt was 820 g. The titer for the xylanase mixture was 35 IU xylanase/ml. The buffer consisted of 150 ml of 50 mM phosphate, pH 7.0. The balance of the reaction mixture was water. Enzyme loading rates were 13.13 or 5 IU/g OD pulp.

Duplicate samples of pulp (820 g wet) in a plastic bag, buffer (150 ml), and water (530 ml for enzyme treatment; 550 ml for control) were each equilibrated separately at 60° C. The enzyme was kept on ice until just before the pulp treatment was initiated. Treatment was started by diluting the enzyme in the pre-equilibrated buffer and water, and adding the enzyme solution to the pre-equilibrated pulp with simultaneous mixing. Controls were performed in a similar manner but with water substituted for enzyme. The pulps were periodically mixed by kneading the bags during 3 hours of incubation at 60° C. Following incubation, the pulps were dewatered on a Buchner filter, washed and preheated to 65° C. prior to the addition of 1.5 g NaOH per 150 g OD pulp (1% NaOH by wt, 5% consistency). The pulps were extracted for 1 hour at 65° C., dewatered by filtration on a Buchner funnel and washed repeatedly with 60° C. water until the wash waters were neutral.

The kappa content of the pulp was reduced by the enzyme treatment as shown in the following table:

TABLE 2

| sample | Enzyme treatment | kappa number |
|---|---|---|
| Starting pulp | none | 16.3 |
| Control | none | 16.0 (after extraction) |
| Sample | 5 IU/g OD | 13.04 (after extraction) |

Therefore, enzyme treatment reduced the kappa number by 18.5% in comparison to the control. The chlorine demand should be reduced by an equivalent amount.

c. Xylanase enhancement of oxygen bleaching of a hardwood kraft pulp. 150 g OD of eastern hardwood pulp was treated as according to the procedure in Example 4(b). Following enzyme treatment and alkali extraction, the pulps were bleached with an elemental chlorine-free bleaching sequence that employed sodium hydroxide (2.25% on an OD basis) plus hydrogen peroxide and 1.1% chlorine dioxide ($ClO_2$).

Results were as follows:

TABLE 3

| Sample | Enzyme treatment | kappa number | Viscosity (cps) | Final brightness |
|---|---|---|---|---|
| Starting pulp (hardwood) | none | 17.0 | ND | ND |

TABLE 3-continued

| Sample | Enzyme treatment | kappa number | Viscosity (cps) | Final brightness |
|---|---|---|---|---|
| Control (following bleaching) | none | 16.1 | 56.0 | 76.9 |
| Enzyme-treated (following bleaching) | 5 IU/g OD | 14.5 | 56.4 | 81 |

Enzyme treatment therefore increased brightness and viscosity of oxygen-delignified kraft pulp while reducing kappa.

d. Xylanase enhancement of a chlorine bleach sequence for southern pine kraft pulp.

In this example, the material consisted of 150 g OD of southern pine kraft pulp treated as in Example 4 (b) above. The resulting sample and control pulps were subjected to a 50% reduced $Cl_2$ bleaching sequence (i.e., only half of the standard amount of elemental chlorine was employed). The bleach sequence employed was as follows: CEHED where C is elemental chlorine ($Cl_2$); E is alkali (1%); H is hydrogen peroxide (0.5%) and D is chlorine dioxide ($ClO_2$). Brightness can be measured by several standards and test methods including Tappi Standard T 217 M-48, T 218 OS-75, SCAN-C 11:75 or ISO 3688–1977 E). The most commonly used brightness value represents the reflectance value of blue light at 375 or 360 nm of a pulp sheet (in %) based on the reflectance of magnesium oxide as a standard sample. ISO brightness values were used unless otherwise stated. The results were as follows:

TABLE 4

| Sample | kappa number | Bleached Brightness |
|---|---|---|
| Initial pine kraft pulp | 25.9 | ND |
| Control pine kraft pulp following alkali extraction | 22.56 | ND |
| Enzyme-treated pine kraft pulp following alkali extraction | 22.12 | ND |
| Control following bleaching (duplicate samples) | ND | 76.0 / 76.0 |
| Enzyme-treated following bleaching (duplicate samples) | ND | 79.9 / 79.9 |

Therefore, the brightness of the pulp was enhanced with enzyme treatment. In the same manner, we also obtained an enhanced bleaching effect for eucalyptus pulp.

e. Enhancement of chlorine bleaching by enzyme treatment, alkali and hydrogen peroxide extraction.

Softwood (pine) kraft pulp with an initial kappa of 29, a brightness of 32 and a viscosity of 20 was treated with 5 IU/g OD of a mixture of the four xylanases and subsequently extracted with either alkali (1%, OD pulp basis) or 1% alkali plus hydrogen peroxide (0.5%, OD pulp basis). Control pulps were extracted with either alkali or alkali plus peroxide as in the test condition, but were otherwise unaltered. Following enzyme and alkali or alkali plus peroxide treatments, pulps were bleached with chlorine using 10% chlorine dioxide substitution (CD) at one of four levels. The total amount of active chlorine used was equal to the lignin content as determined by micro kappa (k) multiplied by 0.18, 0.14, 0.10 or 0.06. The amount of sodium hydroxide employed in the E1 was equal to the active chlorine multiplied by 0.55. Similar calculations were employed in the D1 and D2 stage treatments with chlorine dioxide. E1p and E2p extractions used 1% NaOH plus 0.5% $H_2O_2$.

Figure 7:
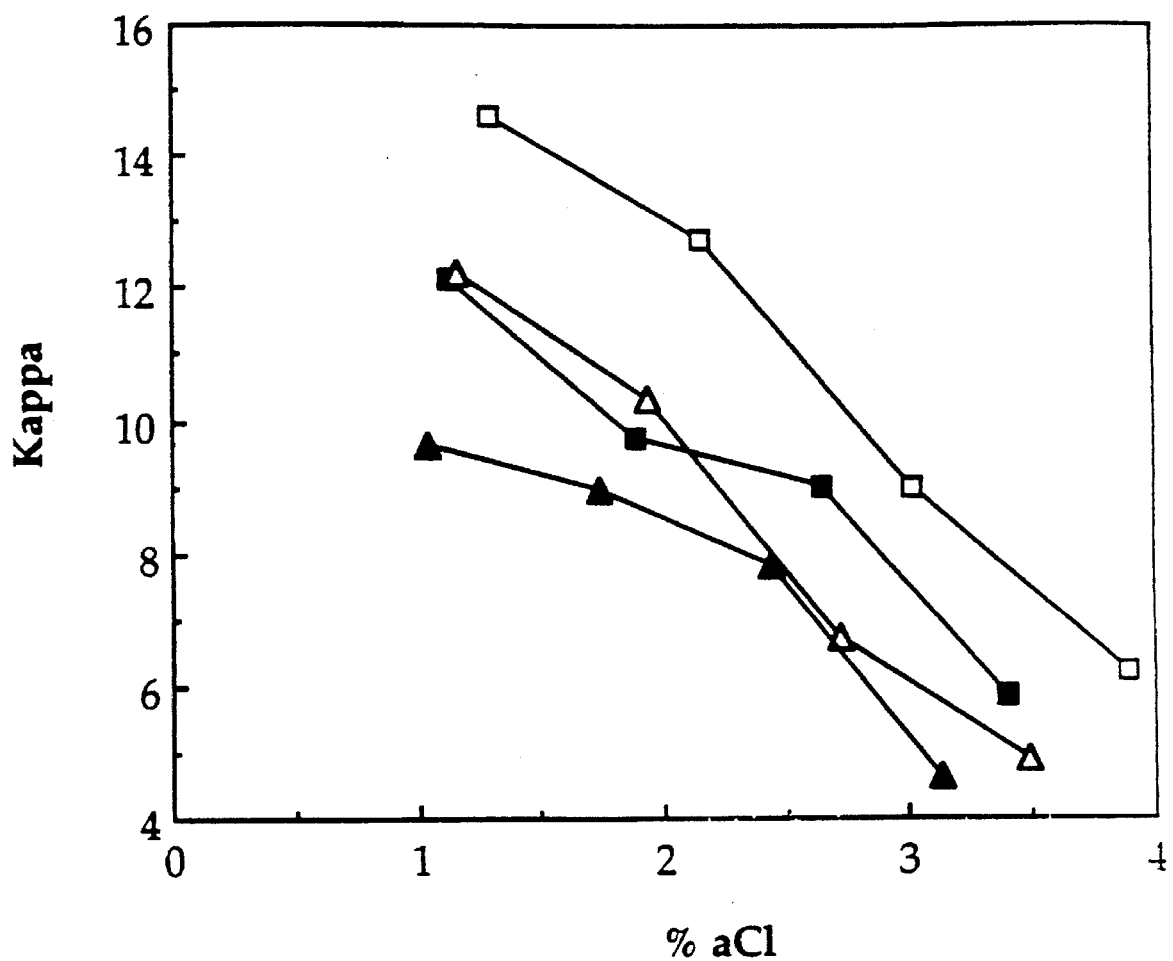
FIG. 7 is a graph of the effect of alkali, xylanases, and hydrogen peroxide on the chlorine requirement for bleaching a softwood kraft pulp.
Figure 8:
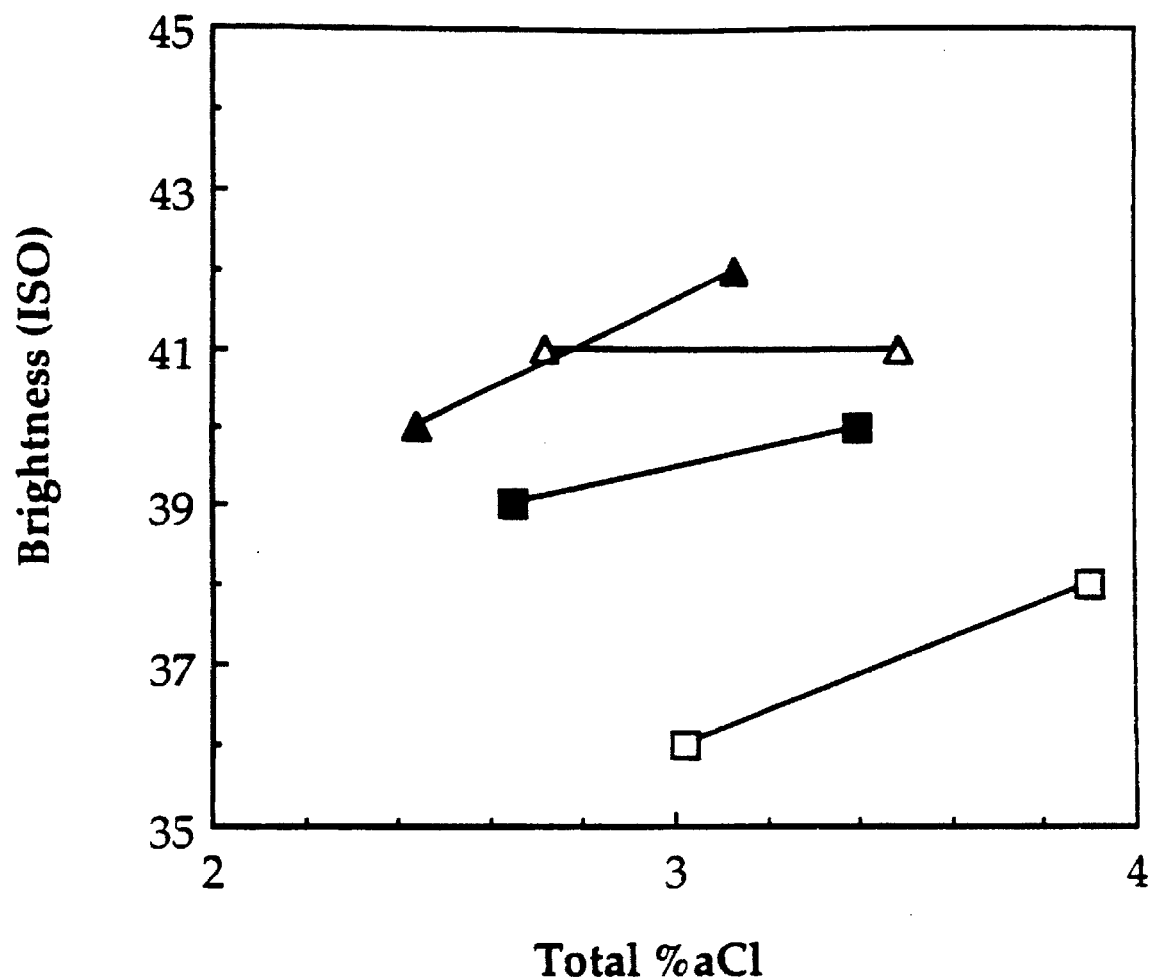
FIG. 8 is a diagram of the effects of the xylanases, alkaline extraction and hydrogen peroxide on the brightness of the softwood kraft pulp.

The results are reported graphically in the following FIGS. 7 and 8. It can be seen that enzyme treatment reduced the amount of chlorine required to attain a target kappa of 7 by about 30%. Hydrogen peroxide also reduced the amount of chlorine required, and the combination of enzyme with peroxide was particularly effective at low levels of NaCl.

5. Chromophore removal.

Figure 9:
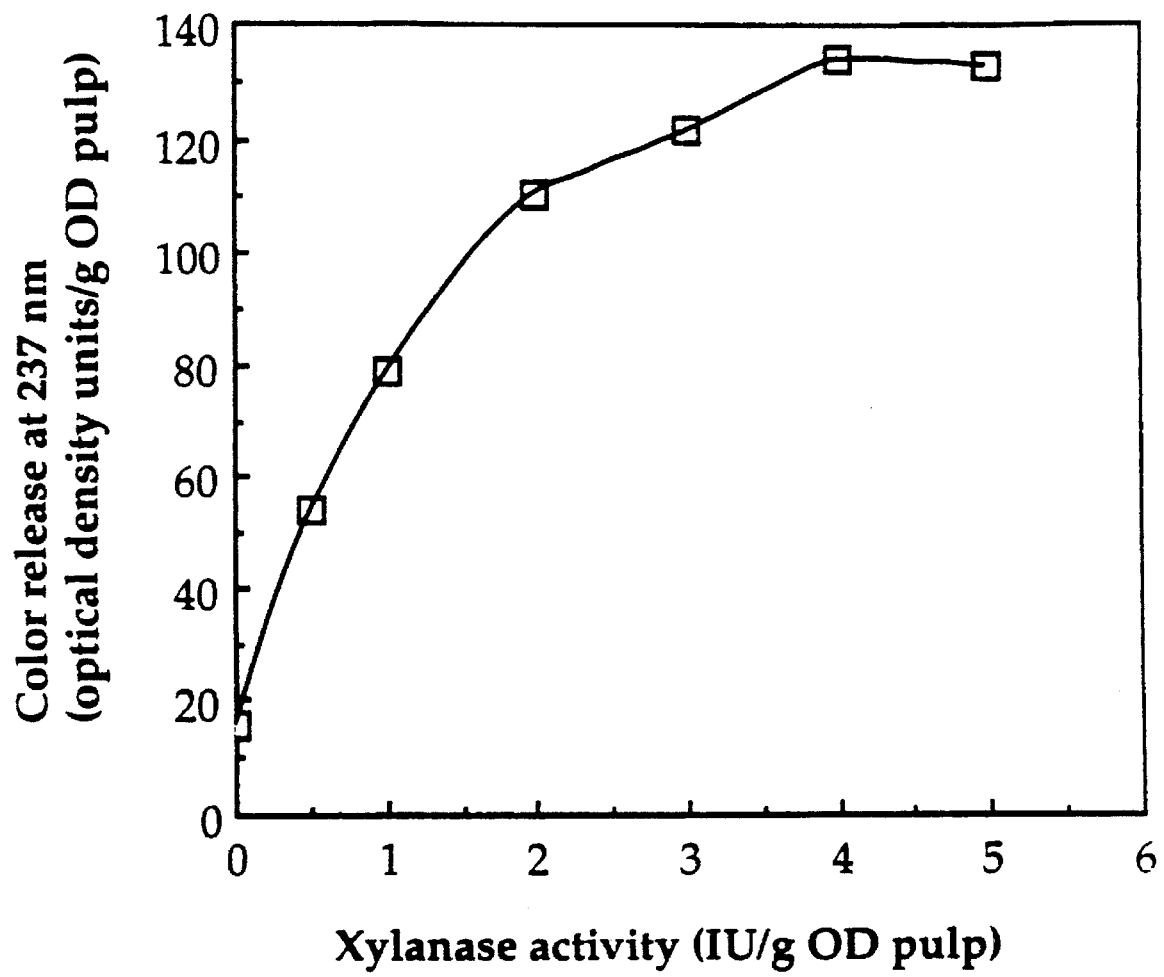
FIG. 9 is a diagram of chromophore release, as measured by absorbance at 237 nm, versus xylanase concentration.

Beyond the ability to reduce the kappa number and enhance bleaching, however, the xylanases actually remove color from the pulp (FIG. 9). This is a characteristic not observed with other xylanases known to enhance bleaching. A southern red oak kraft pulp was treated with crude xylanase from *S. roseiscleroticus* at various enzyme levels, and the amount of color removed was determined spectrophotometrically at 237 nm. The pulp was treated with enzyme as per Example 4(b) except that 10 mM phosphate buffer, pH 7.0 was employed, and enzyme dosing levels ranged from 0 to 5 IU/g OD. The results are summarized in FIG. 9. Color removal by the xylanases from *S. roseiscleroticus* is essentially linear with enzyme dose up to about 3 IU/g OD of pulp thereby indicating that the enzyme, and not some other factor, is responsible for color release.

We analyzed the ability of other xylanases to release chromophores. In a direct comparison of several xylanase preparations when each was tested at the same loading rate on pulp, the *S. roseiscleroticus* xylanases removed significant amounts of color, whereas the xylanase preparations from *Trichoderma reesei*, and *Aureobasidium pullulans* did not. No other fungal xylanase we analyzed released chromophores.

Figure 10:
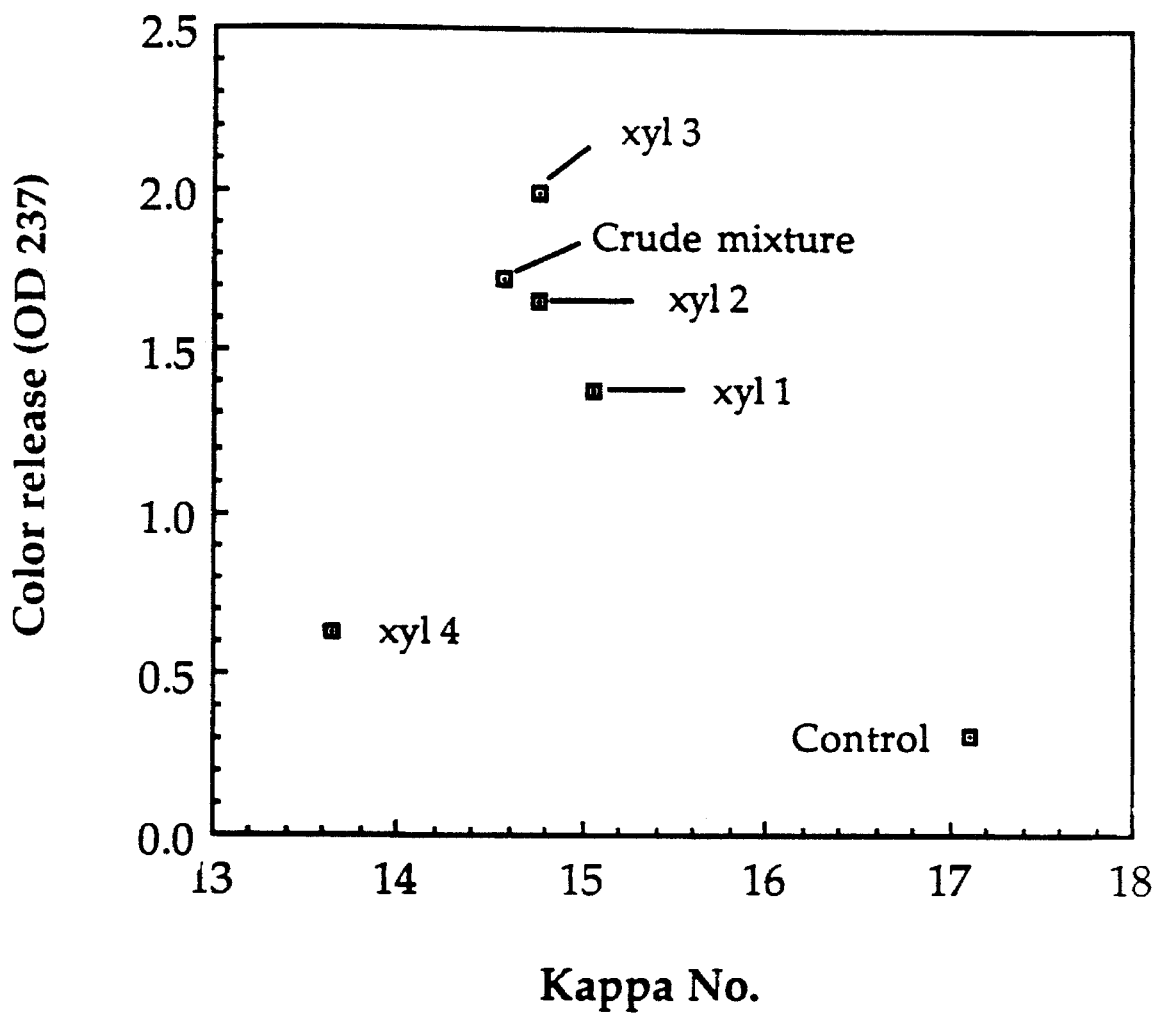
FIG. 10 is a diagram comparing chromophore release, as measured by absorbance at 237 nm, versus resulting kappa number of the pulp after extraction with alkali for the four different xylanases and the xylanase mixture.

At least two of the xylanase fractions were able to release color when acting alone. Samples of southern red oak kraft pulp were treated with 5 IU/g OD of purified xylanase isoenzyme fractions under conditions employed above. The release of chromophores was determined by spectroscopy at 237 nm, and the resulting kappa numbers of the pulps following extraction with 1% alkali at 65° C. for 1 hour were measured. For comparison, the color release and kappa number of a control pulp not treated with enzyme is also shown. FIG. 10 describes these results.

FIG. 10 shows that xyl 4 results in a relatively greater reduction in kappa per unit of enzyme activity employed and that xyl 3 results in relatively greater release of color. As is shown in FIG. 10, 5 IU/g of xyl 3 alone was able to release even more color than the mixture of xylanases when applied at the same dosing level. Some color was released by the buffer alone, but this was significantly less than that released by the enzymes.

The xylanases of the present invention are capable of releasing chromophores from secondary fiber pulps. We used the xylanases to enhance color removal and kappa reduction of old corrugated containers prepared from softwood secondary fiber. A pulp with an initial kappa of 86 was prepared from old corrugated containers (OCC) and divided into two batches. One batch was soaked in alkali (10%, OD pulp basis) at room temperature for 4 hours; the other batch was used without further treatment. The control OCC and the alkali-treated OCC were each treated with 5 IU of xylanase/g OD pulp under the standard conditions, and the resulting supernatant solutions were recovered and assayed for absorbance at 237 and 280 nm. Effectiveness was determined by multiplying the volume of the solution times the absorbence at each wavelength (optical density ml=OD units). FIG. 11 graphically illustrates the results. As seen in FIG. 11, the enzyme treatment was particularly effective in removing chromophores absorbing at 237 nm.

Figure 12:
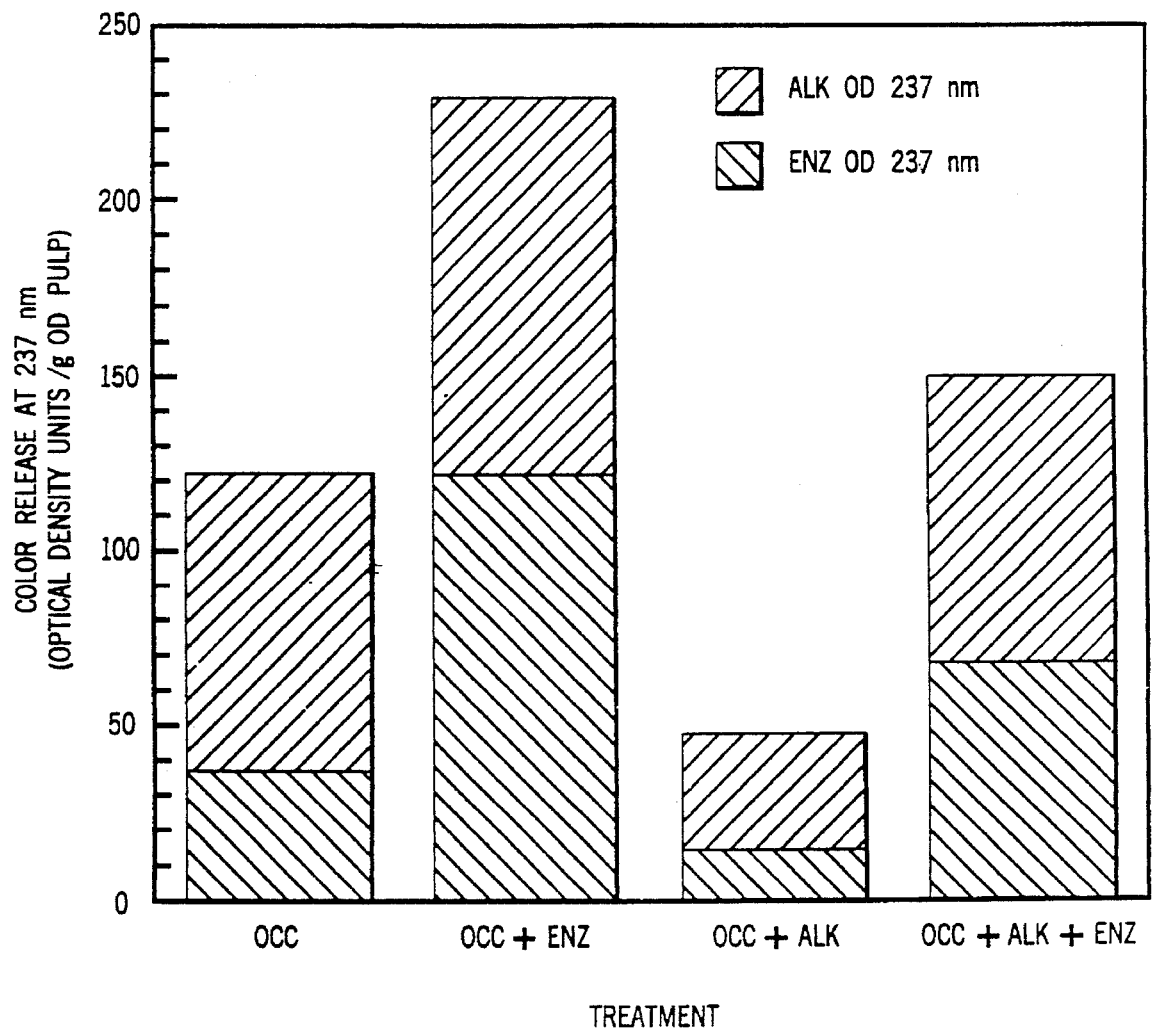
FIG. 12 is a diagram comparing chromophore release and various pulping treatments involving old corrugated containers and alkali extraction.

Enzyme treatment also facilitated the subsequent extraction of chromophores by 1% alkali as is shown in FIG. 12.

Notably, enzyme treatment enhanced 1% alkali extraction of material absorbing at 237 nm even when the OCC had previously been subjected to extraction with 10% alkali. In all instances removal of chromophores was greater with enzyme treatment than without.

FIG. 12 illustrates chromophores released into solution from OCC by enzyme treatment alone (solid bars) or following extraction with 1% alkali (hatched bars). Referring to FIG. 12, OCC=Old corrugated containers; OCC+Enz= pulp that had been treated with enzyme prior to extraction with 1% alkali; OCC+Alk =OCC that had been treated with 10% alkali prior to a second extraction with 1% alkali; OCC+Alk+Enz=OCC that had been treated with 10% alkali, followed by enzyme treatment, followed by extraction with 1% alkali.

Figure 13:
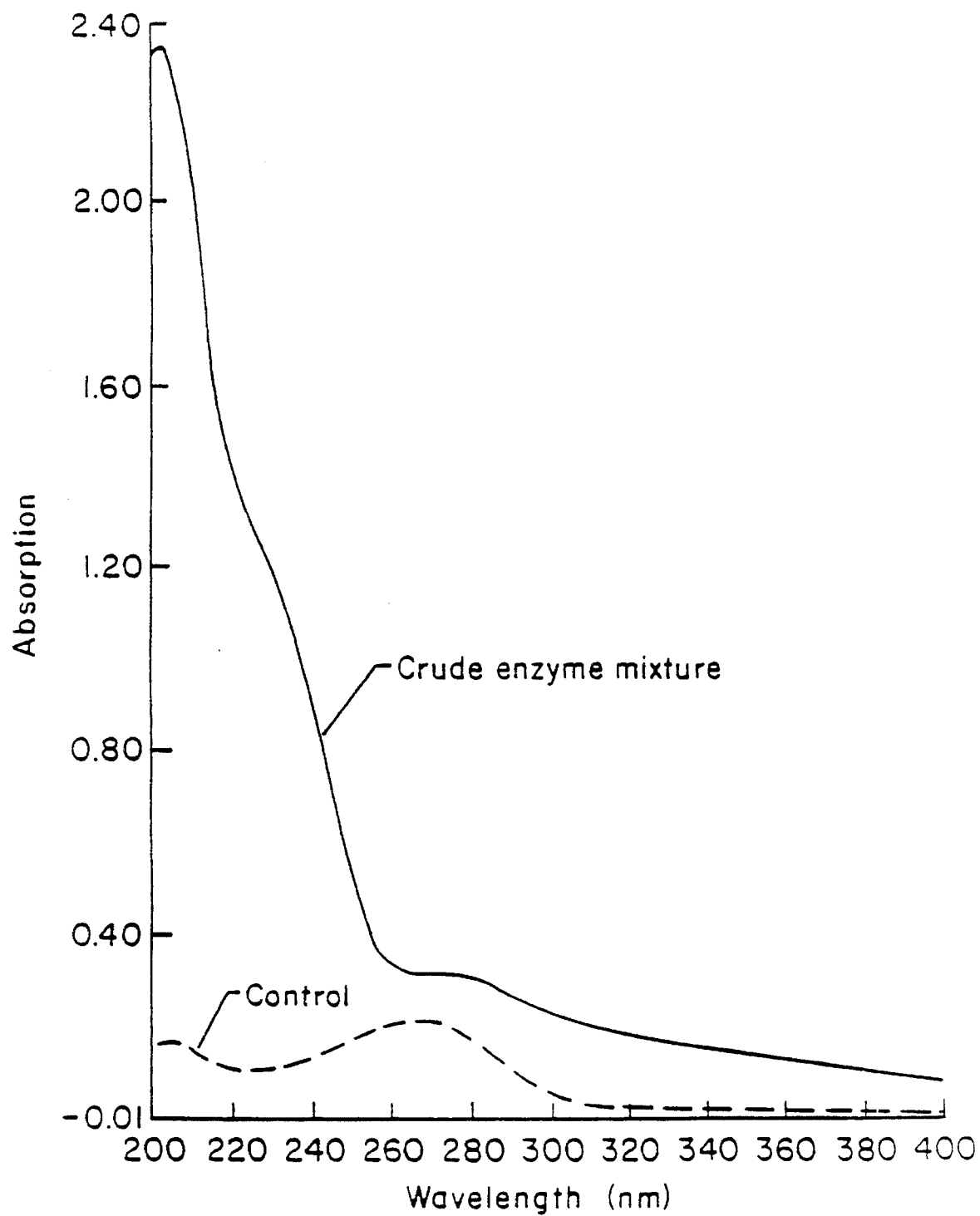
FIG. 13 is an absorption spectrum of the colored material removed by the xylanases compared to the absorption spectrum of material removed by buffer alone.

We have partially characterized the nature of the chromophores by UV/visible spectroscopy. The absorption spectrum of the chromophores does not correspond to a characteristic spectrum for lignin, i.e. there is no absorption peak at 280 nm (FIG. 13).

Figure 14A:
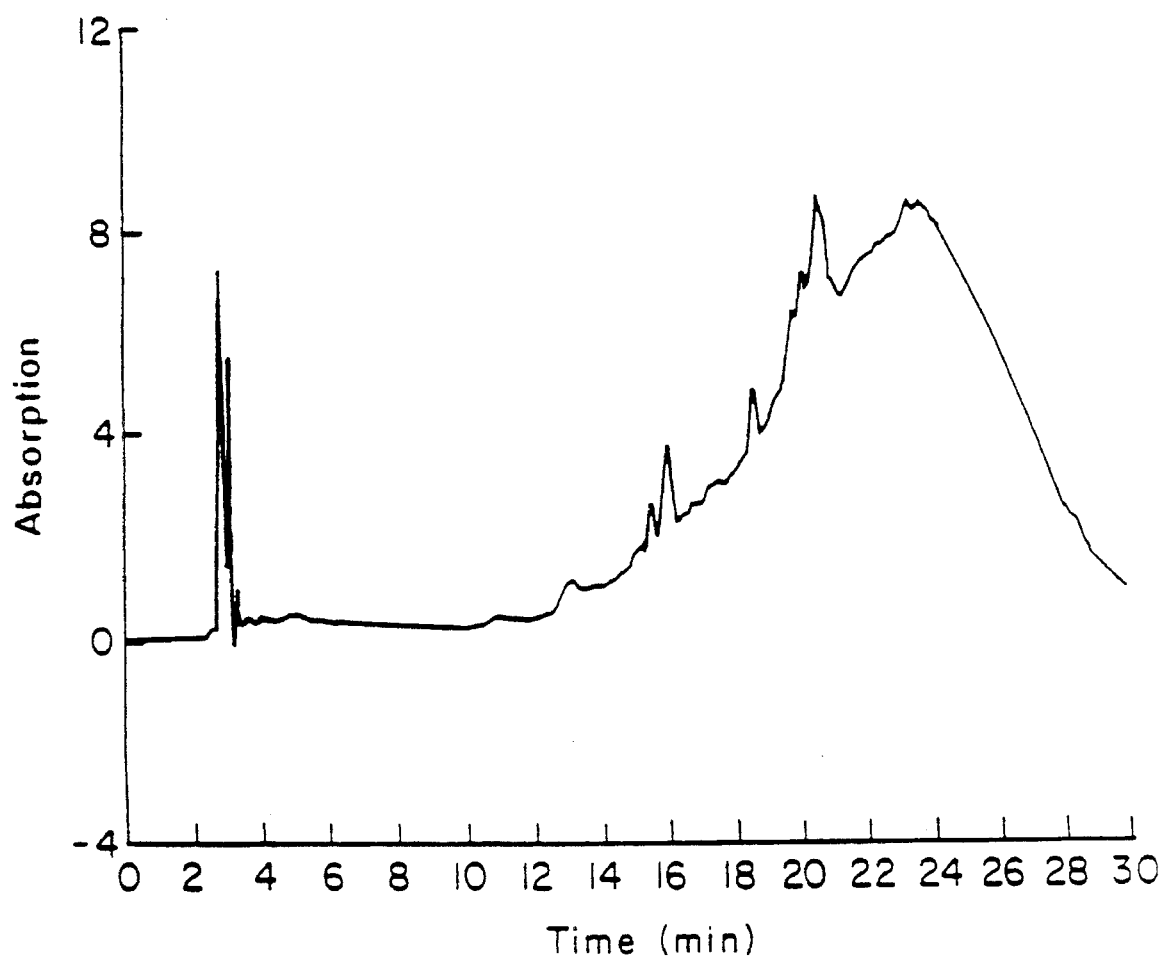
FIG. 14 (A) and (B) illustrates the absorbance of the chromophores in the ultraviolet (B) and visible regions (A) following their separation by reverse phase liquid chromatography.
Figure 14B:
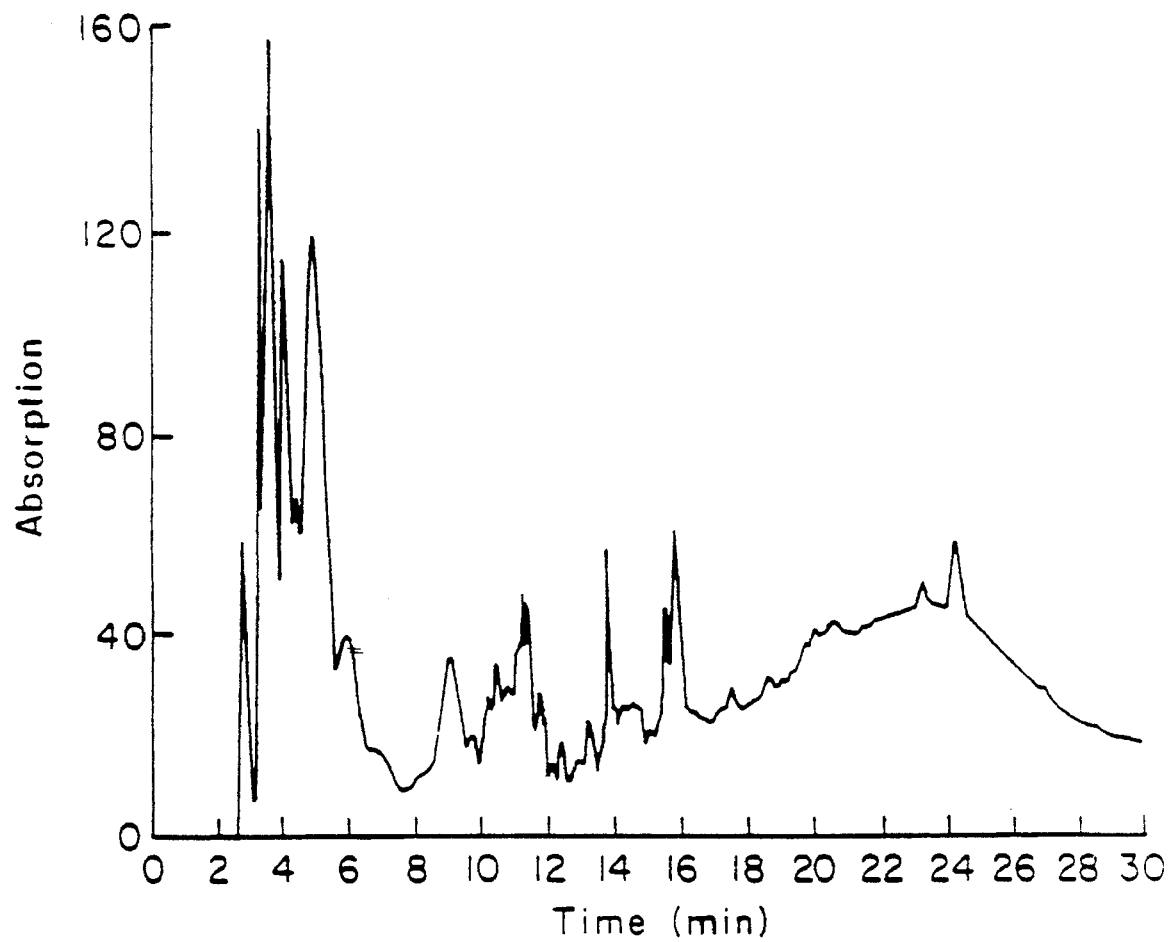
Figure 15A:
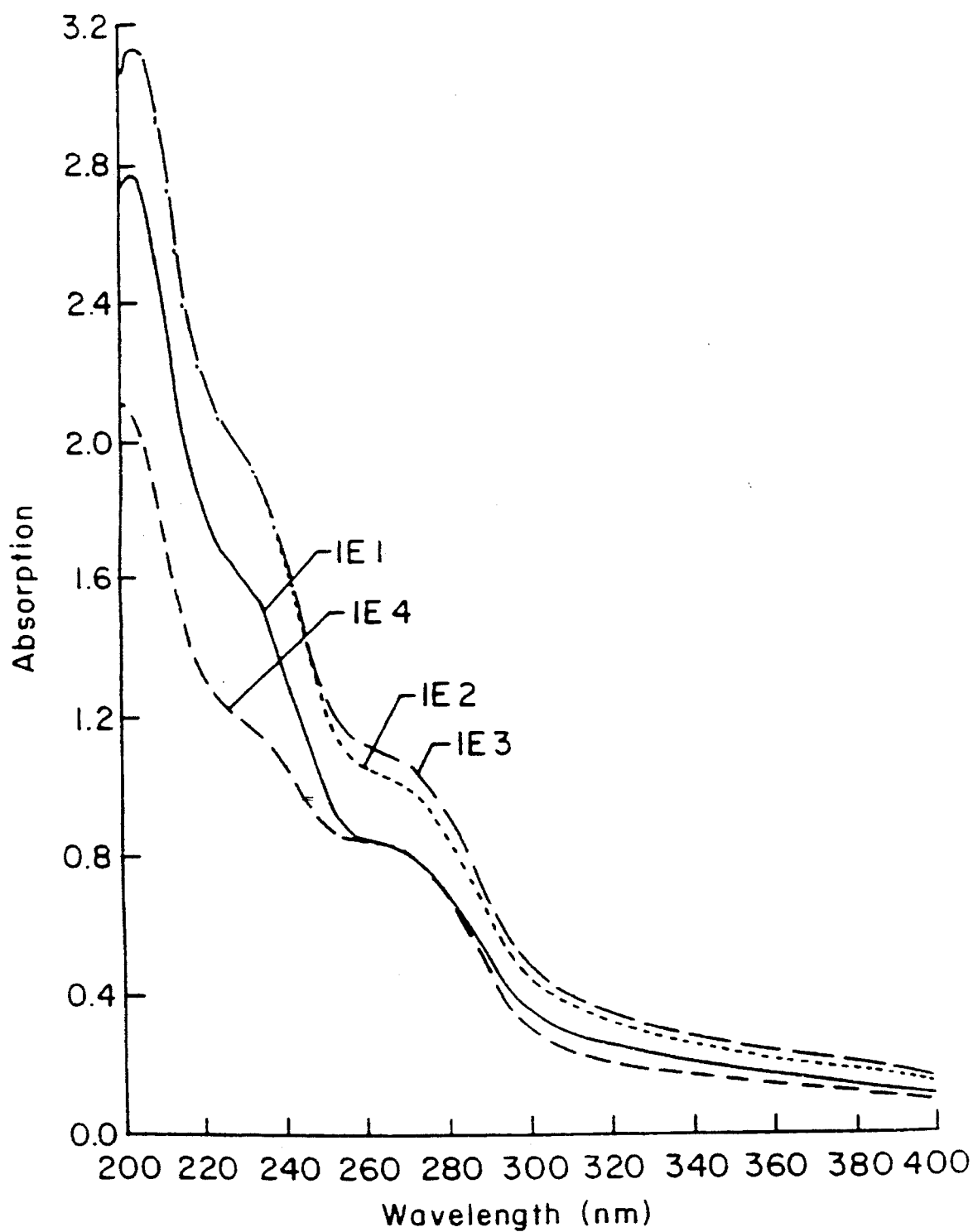
FIG. 15 (A) and (B) are UV spectra of chromophores released during enzymatic treatment (A) and following alkali extraction (B).
Figure 15B:
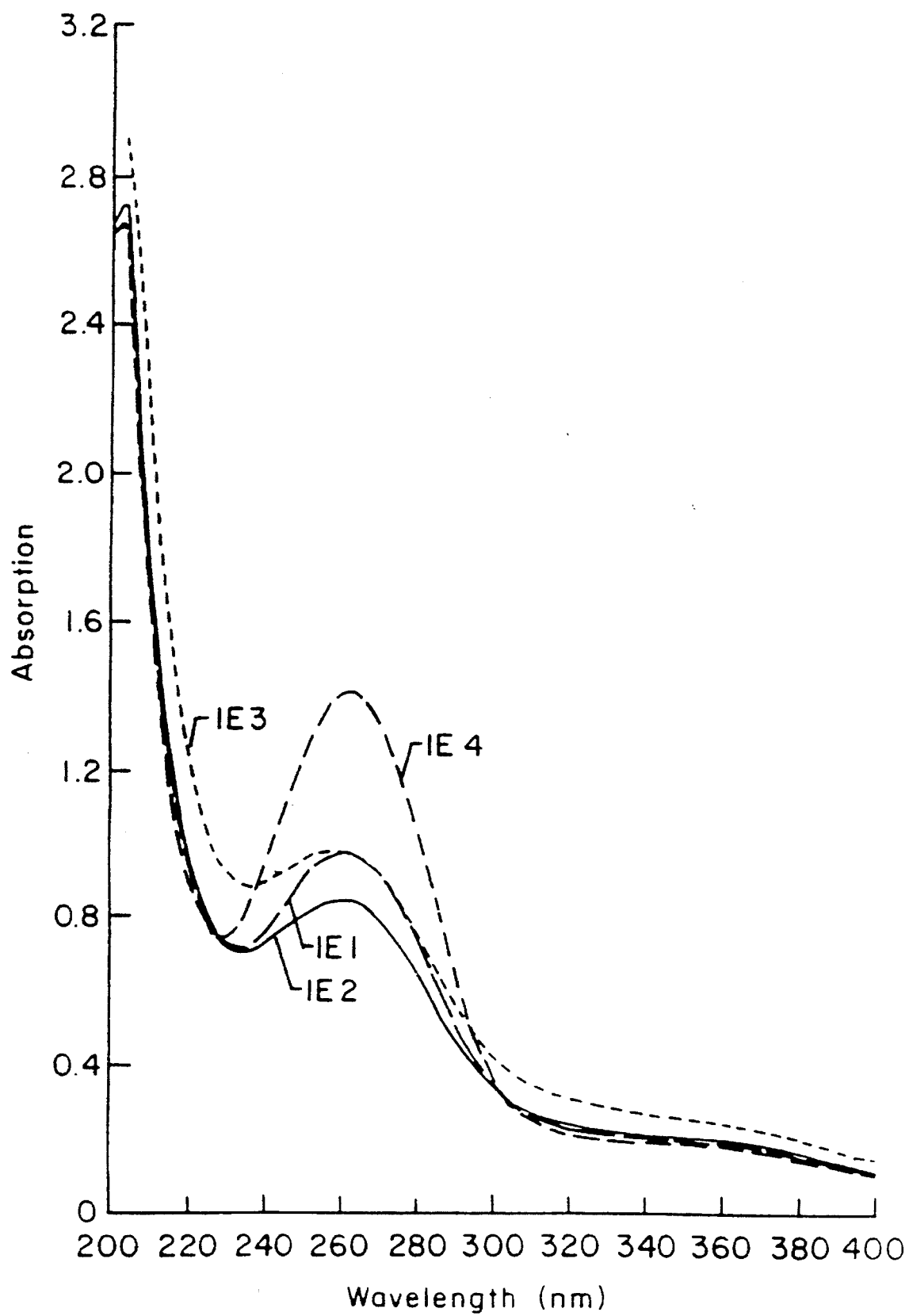

We also fractionated the chromophores using a reverse-phase HPLC column that separates the products on the basis of their hydrophobicity. The most hydrophobic compounds are eluted last under the conditions of this separation. We employed a diode array detector to determine the adsorption characteristics of each product peak as it emerged from the column. Two broad-band adsorptions were employed: one in the UV region and one in the visible region. A total of more than 40 product peaks were observed. (FIG. 14) Strong UV adsorption was observed in most of the peaks, but especially in products eluting near the start of the run (more hydrophilic materials). Many fewer products were observed to absorb in the visible region. Most of these were more hydrophobic, i.e., they eluted later. FIG. 15 illustrates the UV spectra of chromophores released during enzymatic digestion (A) and following alkali extraction (B).

6. Identification of Other Isolates that express Xylanases Capable of Removing Chromophores.

Several additional novel xylanase-expressing isolates were obtained and screened in the manner described above. The enzymatic activities of crude enzyme preparations were compared with those of *Streptomyces roseiscleroticus*. Other isolates were obtained from a culture collection (Dr. George Szakacs, Technical University of Budapest, Budapest, Hungary). The enzymes were compared for pH optima, pH stability and temperature stability. Results with the best isolate from our screening program, which we named J2-5, and with two thermophilic isolates from the Budapest collection (*Streptomyces thermonitrificans* TUB B-236 and Streptomyces sp. TUB B-12-2) are described below.

Figure 16:
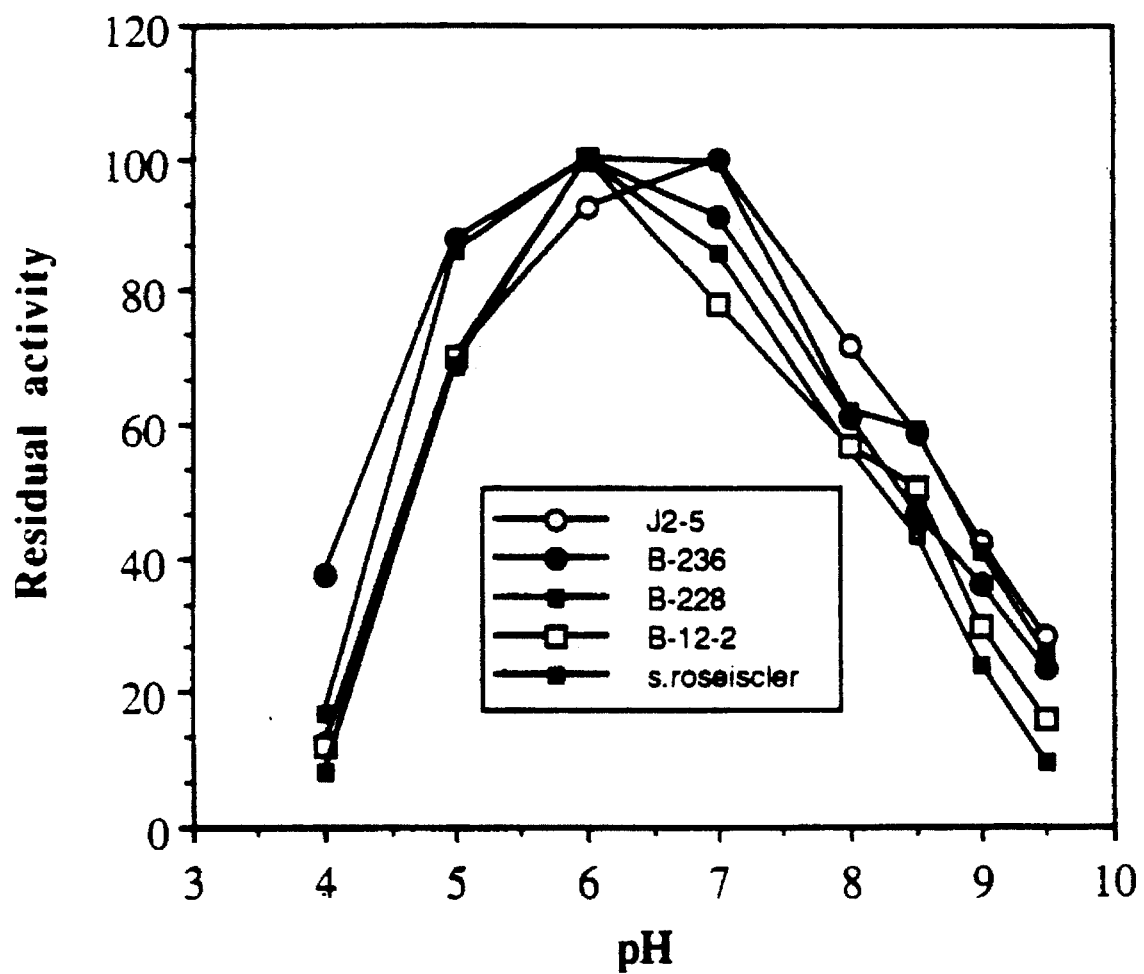
FIG. 16 is a diagram comparing the pH optimum of different crude xylanase preparations from *Streptomyces thermonitrificans* TUB B-236 and *Streptomyces lusitanus* TUB B-228, Streptomyces sp. J2-5 and Streptomyces sp. TUB B-12-2, and *Streptomyces roseiscleroticus*.

We consider a xylanase to have an alkaline pH activity if at least 10% of the enzyme activity present at the optimum pH is still present at pH 9. As can be seen from FIG. 16, about 40% of the activity present at the optimum pH with the crude xylanases from J2-5 and *S. roseiscleroticus* had about 40% of their residual activity at pH 9. Xylanases from B-236 and B-12-2 had relatively less activity at this pH, but still had alkaline pH activity.

Figure 17A:
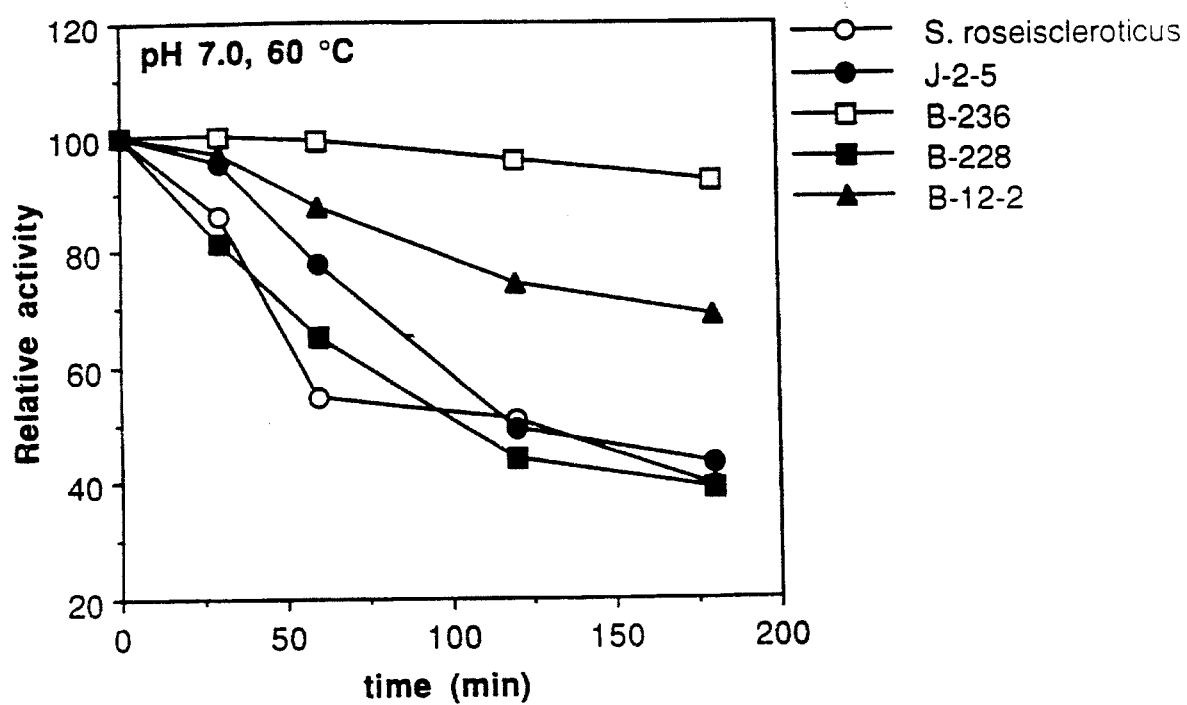
FIG. 17 (A), (B) and (C) is a set of three diagrams comparing the stability of xylanase preparations at pH 7.0, 60° C.; pH 8.5, 60° C.; and pH 7.0, 65° C.
Figure 17B:
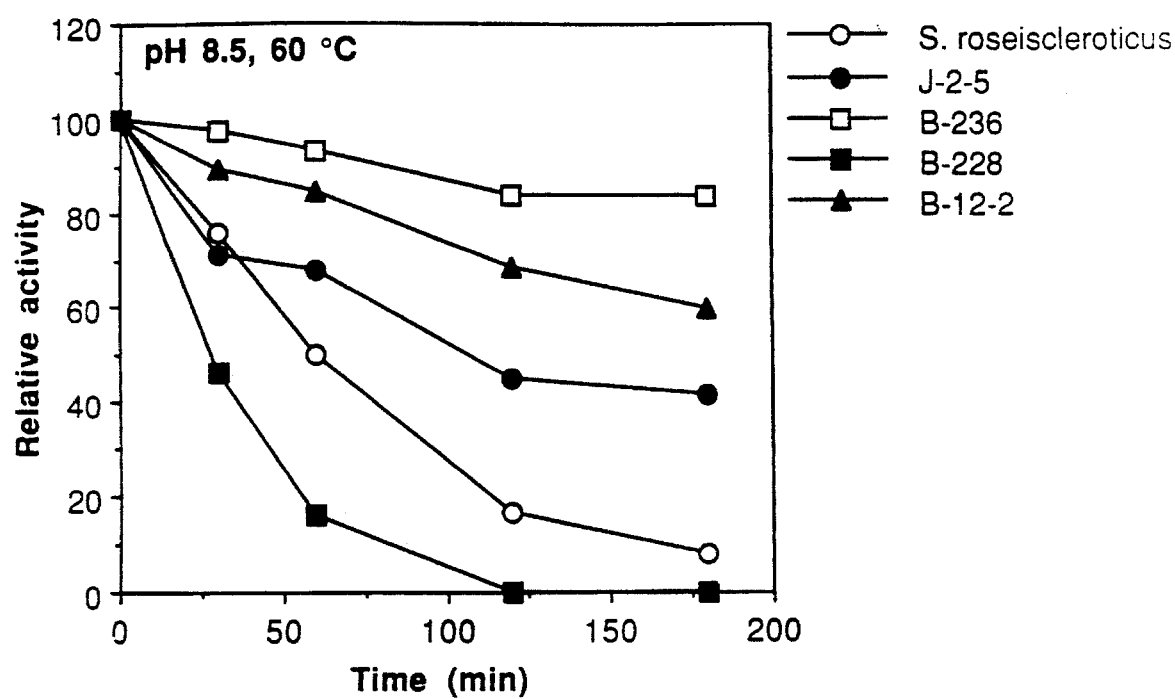
Figure 17C:
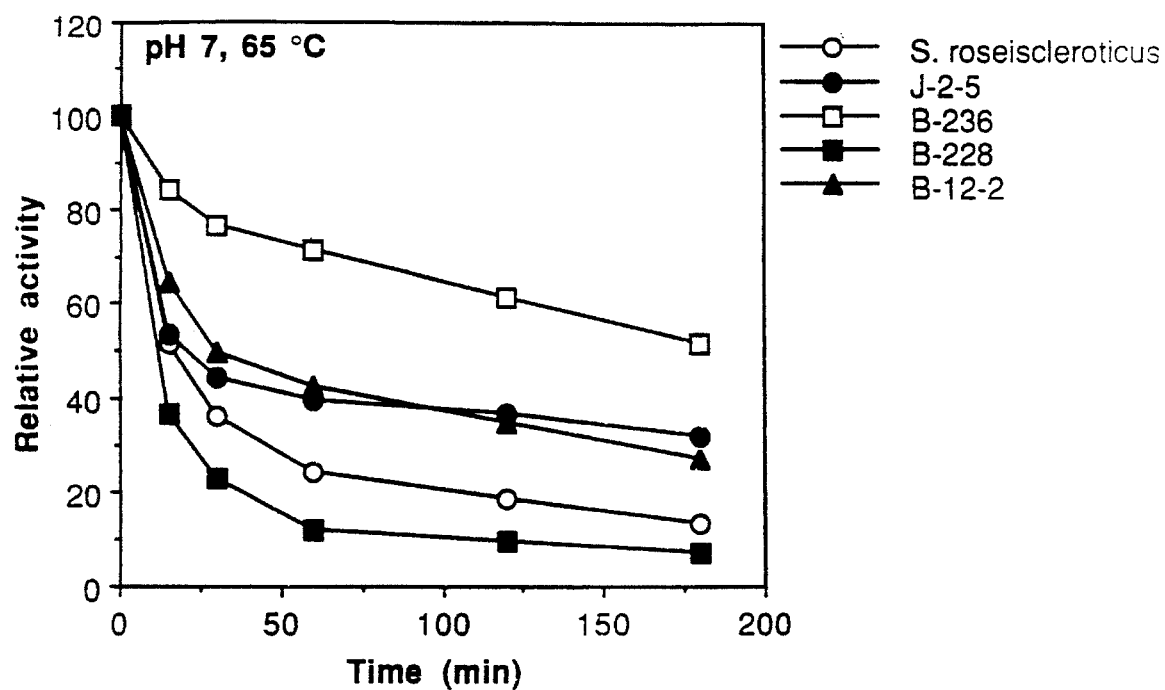

An enzyme should have thermal stability at an alkaline pH in order to operate at best advantage under the conditions described. Therefore, we tested the thermal stability (at 60° C.) of these preparations at pH 7.0 and 8.5. As can be seen in FIG. 17 (*a, b, c*), the xylanase preparation from B-236 showed good stability at 60° C. at both pH 7.0 and 8.5. In both instances, the second-most stable enzyme was from B-12-2. As can also be noted from FIG. 17, B-236 showed acceptable thermal stability even at 65° C., pH 7.0.

Figure 18:
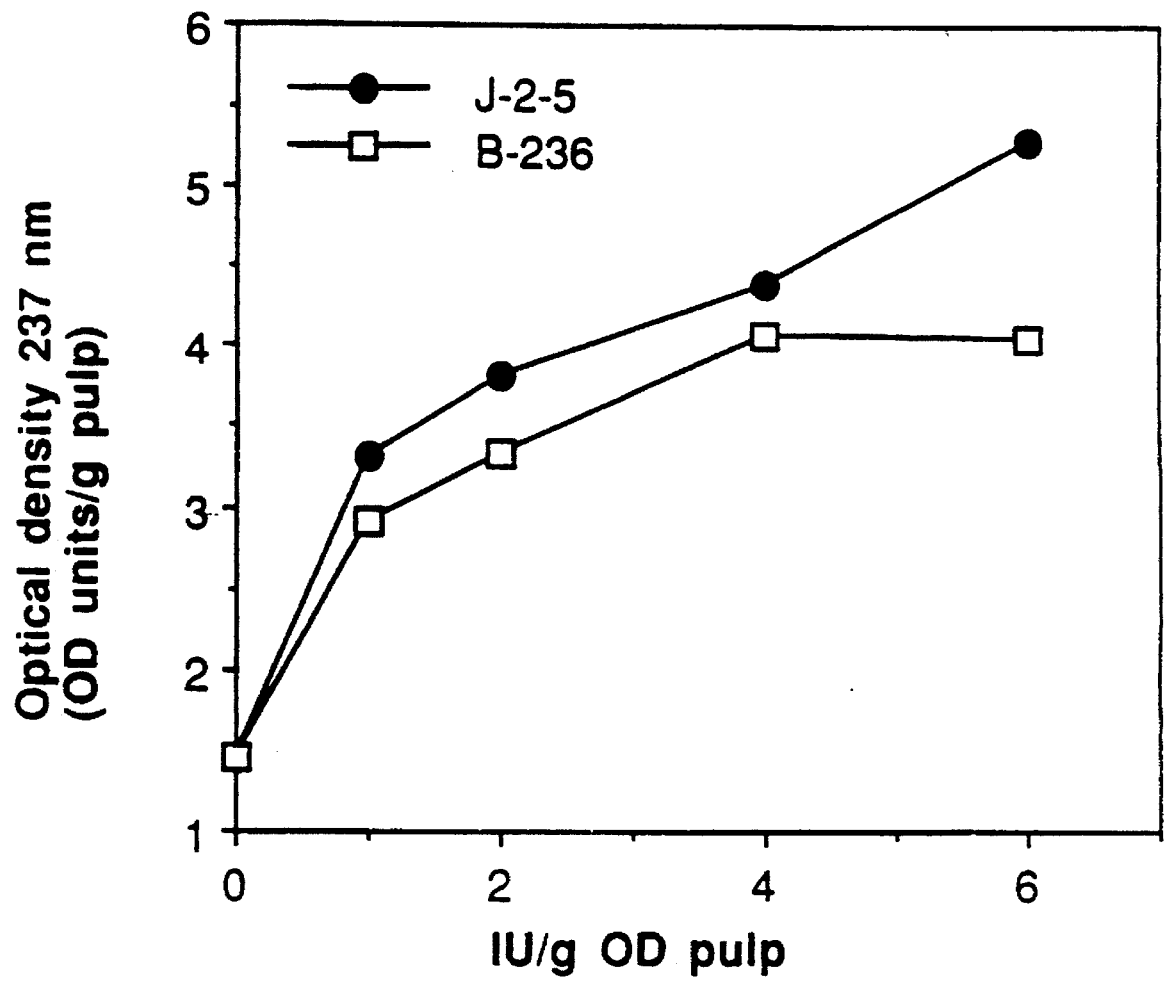
FIG. 18 is a diagram comparing chromophore release from two xylanase preparations.

Crude enzyme preparations from J2-5 and B-236 were compared for their abilities to release chromophores at pH 7.0, 60° C. The results are shown in FIG. 18. As can be observed, both preparations were able to release chromophores from a softwood pulp. The enzyme from J2-5 was slightly more effective than that from B-236.

Crude enzyme preparations from J2-5, B-236 and B-12-2 were compared as to their ability to reduce kappa, increase viscosity and release chromophores as a function of increasing enzyme amount (IU/g). The following Table 5 summarizes the color release, the kappa number, and the viscosity following alkali extraction of oxygen-delignified softwood kraft pulp at pH 7.0 by the crude enzyme preparations. In this particular instance, 10% alkali was used rather than the 1% alkali used previously. All other conditions for color release were the same as above. Color release was measured at 237, 280, and 465 nm.

TABLE 5

| Enzyme | IU/g pulp | Kappa no. | Decrease (%) | OD 237 released/g pulp | Viscosity |
|---|---|---|---|---|---|
| Control | 0 | 14.7 | 0 | 14.6 | 22.52 |
| J2-5 | 1 | 12.3 | 16.3 | 33.1 | 22.61 |
|  | 2 | 12.5 | 15.0 | 38.0 | 22.0 |
|  | 4 | 13.3 | 9.5 | 43.9 | 21.17 |
|  | 6 | 11.4 | 22.5 | 52.9 | 19.65 |
| B-236 | 1 | 12.5 | 15.0 | 29.1 | 22.33 |
|  | 2 | 12.7 | 13.6 | 33.3 | 23.87 |
|  | 4 | 12.5 | 15.0 | 40.6 | 20.96 |
|  | 6 | 11.5 | 21.8 | 40.5 | 22.44 |
| B-12-2 | 6 | 10.5 | 28.5 | 54.7 | 23.31 |

The xylanase preparation from B-12-2 resulted in the greatest chromophore release, the greatest decrease in kappa, and one of the highest pulp viscosities. A high viscosity is an indicator of pulp strength and is therefore desirable.

The softwood pulp chromophore-release experiment of Table 5 was repeated, but treatment was carried out at pH 8.5, 60° C. for 1.5 hours, rather than at pH 7, 60° C. for 3 hours. Alkali extraction was performed with 1% NaOH (w/w) at 65° C. for 1 hour. Kappa number and viscosity were measured after alkali extraction while chromophore release was measured after the enzyme treatment. As is shown in Table 6, the B-12-2 enzyme preparation also performed particularly well at pH 8.5.

TABLE 6

| Enzyme | IU/g pulp | Kappa no. | Decrease (%) | OD 237 rel./g | Viscosity |
|---|---|---|---|---|---|
| Control | 0 | 14.6 | 0 | 13.6 | 24.19 |
| J2-5 | 2 | 13.6 | 6.8 | 39.6 | 23.53 |
|  | 6 | 12.9 | 11.6 | 56.5 | 22.1 |
| B-236 | 2 | 13.5 | 7.5 | 29.8 | 23.2 |
|  | 6 | 13.3 | 7.5 | 43.2 | 23.84 |
| B-12-2 | 2 | 13.1 | 10.3 | 41.1 | 24.48 |
|  | 6 | 13.0 | 11.0 | 51.1 | 25.77 |

Batches of commercial hardwood and softwood pulp were treated with a crude xylanase preparation from B-12-2 at pH 7.0, 60° C. for 3 hours. Alkali extraction and chromophore release determination were carried out as reported above. As shown in Table 7, chromophore release from both pulps increased with increasing enzyme dose under these conditions. Stage 1 is the enzyme treatment. Stage 2 is the alkali extraction. The kappa number decreased significantly in the case of the hardwood pulp. Lesser decreases were observed with the softwood pulp.

TABLE 7

| IU/g OD pulp | Stage 1 Chromophore removal OD units/g pulp | | Stage 2 Chromophore removal OD units/g pulp | | Stage 2 Kappa number |
|---|---|---|---|---|---|
| | 237 nm | 465 nm | 237 nm | 465 nm | |
| hardwood | | | | | |
| 0 | 6.2 | 0.7 | 34.8 | 3.4 | 10.29 |
| 1 | 67.2 | 2.5 | 32.0 | 2.5 | 8.65 |
| 2 | 84.6 | 2.9 | 43.2 | 3.4 | 7.78 |
| 4 | 94.2 | 3.3 | 44.0 | 3.3 | 8.01 |
| 6 | 97.4 | 3.2 | 108.0 | 5.6 | 7.44 |
| softwood | | | | | |
| 0 | 4.8 | 0.2 | 51.6 | 3.3 | 18.05 |
| 1 | 23.6 | 0.7 | 108.0 | 6.0 | 16.74 |
| 2 | 27.4 | 1.0 | 114.3 | 6.2 | 16.71 |
| 4 | 31.4 | 1.2 | 129.2 | 6.5 | 16.92 |
| 6 | 36.2 | 1.5 | 192.7 | 6.5 | 16.33 |

7. Purification of xylanes from Streptomyces sp. TUB B-12-2.

Five substantially purified xylanase isoenzymes were obtained from B-12-2 as follows:

(a) Enzyme production. Streptomyces sp. TUB B-12-2, isolated from soil (Vesima, GE, Italy), was cultivated as previously described by Grabski and Jeffries, *Appl. Environ. Microbiol.*, 57:987–992 (1991) and by Grabski et al., *Protein Expression Purification*, 4:120–129 (1993). Briefly, the strain was cultivated in medium of Morosoli et al. at 45° C. (50 ml/250 ml Erlenmeyer flask) using 1% oat spelt or birch xylan as sole carbon sources. For enzyme production, a spore suspension prepared from a one week-old plate culture was primed by growth in trypticase soy broth (TSB, Difco) at 45° C. with shaking at 250 rpm for 24 hours. A portion (5% v/v) of this culture was used to inoculate 500 ml of xylanase production medium (XPM) in a 2 liter Erlenmeyer flask. XPM employs defined mineral salts with oat spelts xylan as a sole carbon source. Medium components were autoclaved separately from the xylan (12). The average titer, 74 IU/ml (as assayed by DNS), or 20 IU/ml (as assayed by NS) was obtained after 48 hour cultivation on 1% oat spelt xylan. Maximum xylanase activity was generally detected by 48 hours.

Since oat spelt xylan is expensive, various crude xylan-rich substrates were evaluated for enzyme production. Several lignocellulosic materials induced production of extracellular xylanase from B-12-2 to various extents. Among these, ground, sieved corn stalk and wheat straw were the best substrates. Xylanase activity could not be induced by cellulosic substrates (Avicel PH 102 and solka floc), glucose or xylose. However, a small amount of xylanase activity was detected using solka floc SW 40. This activity is probably due to contamination of the cellulose with xylan. Defatted rapeseed meal was a good replacement for both yeast extract and bacto peptone. When 2% ground sieve corn stalk was used in combination with defatted rapeseed meal, xylanase productivity was comparable to that obtained with pure xylan. The level of cellulase activity in the crude preparation (CMCase) was very low (0.08 IU/ml) even when raw lignocellulosic materials were used as a carbon source.

(b) Concentration. Cells were harvested by centrifugation (6,000× g, 30 min). The pellet was discarded and the dark supernatant solution was concentrated 10-fold in a Minitan Millipore ultra-filtration system using a 10,000 mw cut off membrane. Final retentate volume was approximately 100 ml.

(c) Clarification. The retentate was treated with 2 to 3% (v/v) of BPA-1000 in order to precipitate the pigment. This was enough to eliminate about 80% of the color (measured at 392 nm) present in the solution. The pellet was discarded and the clear supernatant was diafiltered with 10 mM Bis/Tris buffer (pH 6.5) in a stirred ultra-filtration cell (Amicon Div., Grace & Co., Danvers, Mass.) equipped with a YM-3disc membrane (3,000 mw cut-off).

(d) Anion exchange. The YM-3retentate was centrifuged at 10,000× g, 10 min. Pellets were discarded and the supernatant, containing 50 to 60 mg of protein/load corresponding to about 1200 IU of xylanase activity, was applied to a Mono Q HR 10/10™ Pharmacia column.

Figure 19:
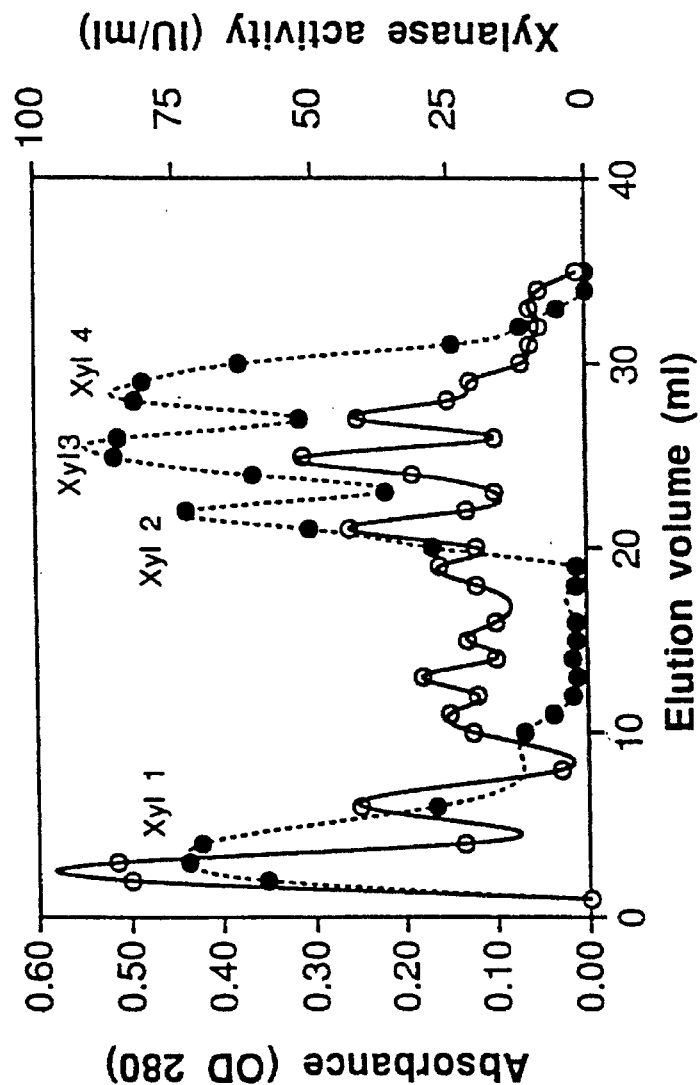
FIG. 19 is a plot of xylanase activity and absorbance at 280 nm of fractions collected from a Mono Q HR 10/10 anion exchange column (Pharmacia). The collected fractions were obtained from a crude enzyme preparation from the thermophilic Streptomyces sp. TUB B-12-2.

Proteins were separated using a discontinuous gradient of buffer A (10 mM Bis/Tris, pH 6.5) and buffer B (Buffer A plus 1.0 M NaCl). The flow rate was 4 ml/min, and 4 ml fractions were collected. Elution was monitored at 280 nm using a UV detector. Xylanase activity was measured using soluble oat spelt xylan using the assay previously reported by Grabski and Jeffries, 1991. Xylanase activity (closed circles) was detected mostly in the unbound fraction (xyl 1) and in three fractions eluting between 120 and 200 mM (xyl 2, 3 and 4; fractions 20 to 30), as is shown in FIG. 19. About 55% of the original activity could be accounted for by summing the activities in fractions following MonoQ separation.

Active fractions were pooled according to their activity and protein chromatogram (open circles), concentrated and diafiltered into 50 mM pH 7.0 potassium phosphate buffer using a stirred ultra-filtration cell as described above.

Figure 20:
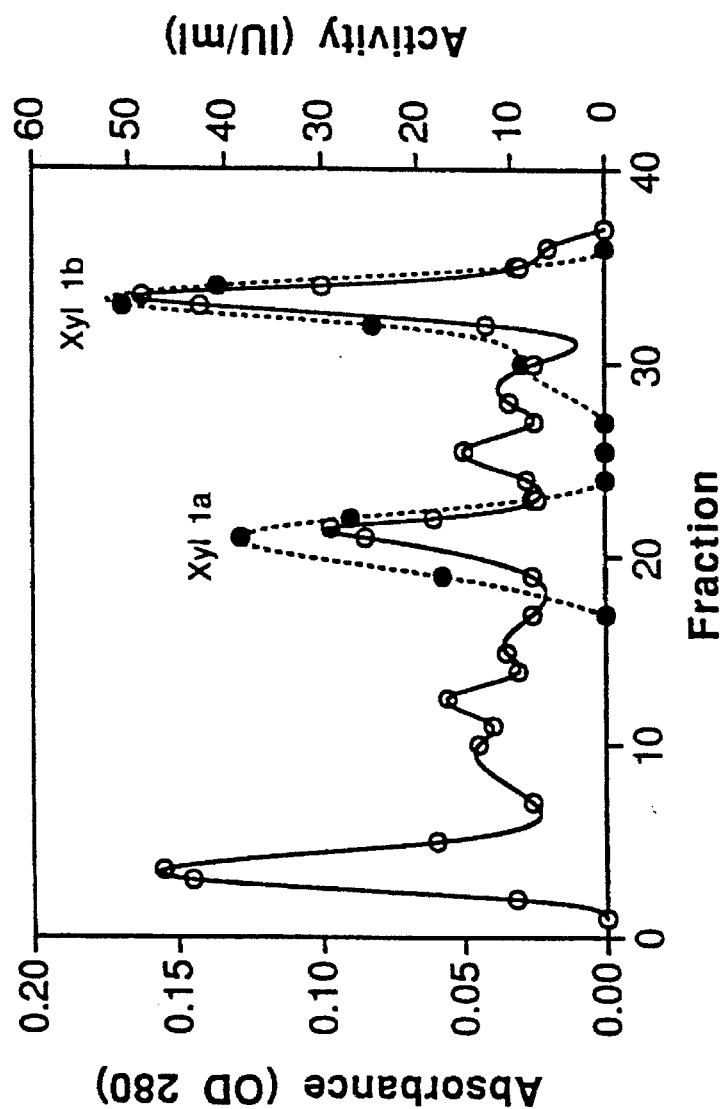
FIG. 20 is a plot of xylanase activity and absorbance at 280 nm of a phenyl superose column separation performed on the material in the xyl 1 peak of FIG. 19 after ammonium sulfate precipitation.

(e) Hydrophobic interaction. Ammonium sulfate was added to the samples to a final concentration of 1.25M. Samples were centrifuged at 10,000× g for 5 min. Pellets were discarded and the supernatant (20 mg protein/load) was applied (0.5 ml/min) to a phenyl superose column. Proteins were separated using a Pharmacia Phast System™ and eluted with a continuous gradient of buffer C (50 mM potassium phosphate pH 7.0+1.25M $(NH_4)_2SO_4$) and buffer D (50 mM potassium phosphate pH 7.0). Elution was monitored at 280 nm and 1 ml fractions were collected. Forty-five percent of the original xylanase activity remained after the phenyl superose column. The fractions containing xyl 1 separated into two isoenzymes, xyl 1a and xyl 1b (FIG. 20). Xyl 3 accounted for about half of the recovered activity. The proteins corresponding to xyl 2, 3 and 4 eluted as essentially homogeneous products (data not shown).

Fractions were pooled according to activity and protein chromatogram. Pooled fractions were concentrated and diafiltered into 50 mM pH 7.0 potassium phosphate using a Centricon-3 (Amicon). Purity of the samples was determined by SDS-PAGE and isoelectric focusing.

The preceding purification steps and yields are summarized Table 8. The xylanases isolated from B-12-2 are named and numbered in accord with the scientific convention in the art. Thus, both *S. roseiscleroticus* and B-12-2 produce enzymes called xyl 1, 2, 3, and 4. They are readily distinguished however by reference to their source organism. Moreover, the physicochemical properties of the xylanases from the two strains differ, as examination of the data presented herein demonstrate.

TABLE 8

| Purification step | Vol. (ml) | Total Protein (mg) | Total activity (IU) | Specific activity (IU/mg) | Yield (%) | Purification (fold) |
|---|---|---|---|---|---|---|
| Crude supernatant | 950 | 1710 | 6650 | 3.9 | 100.0 | 1.0 |
| Concentration | 50 | 590 | 5310 | 9.0 | 79.8 | 2.3 |
| BPA-precipitate | 50 | 236 | 5255 | 22.3 | 79.0 | 5.7 |
| MonoQ-F1 | 50 | 30.2 | 1175 | 38.9 | 17.7 | 10.0 |
| MonoQ-F2 | 25 | 2.8 | 270.3 | 95.8 | 4.1 | 24.6 |
| MonoQ-F3 | 25 | 6.9 | 1550.1 | 225.6 | 23.3 | 57.8 |
| MonoQ-F4 | 25 | 2.9 | 649.2 | 222.3 | 9.8 | 57.0 |
| Phenyl-Superose | | | | | | |
| xyl 1a | 4 | 1.67 | 235.6 | 70.5 | 3.5 | 81.1 |
| xyl 1b | 4 | 2.40 | 468.7 | 194.8 | 7.0 | 49.9 |
| xyl 2 | 4 | 1.05 | 122.8 | 116.5 | 1.8 | 29.9 |
| xyl 3 | 4 | 6.52 | 1531.0 | 234.8 | 23.0 | 60.2 |
| xyl 4 | 4 | 2.80 | 643.0 | 229.6 | 9.7 | 58.9 |

8. Characterization of xylanases purified from B-12-2 a. Basic Physicochemical Characteristics

Physicochemical characteristics of the substantially purified xylanases were determined using the standard techniques outlined below. The physicochemical characteristics are summarized in Table 9.

Xylanase activity was routinely determined by measuring the release of reducing sugars from either 1% (w/v) alkali-soluble or water soluble oat-spelt xylan, using the Somogyi's modification Nelson method (NS) as previously described. Crude or purified enzyme preparations were diluted appropriately to obtain maximal activity consistent with a linear response. For comparative purposes, xylanase activities were measured against 1% (w/v) water soluble and water insoluble xylan from either oat-spelts or birch (Sigma). The dinitrosalicylic acid (DNS) method of Miller, *Anal. Chem.*, 31:426–429 (1959) was used to assay xylanase activity during initial screening. Carboxymethylcellulase activity (CMCase) was assayed by replacing 1% xylan with 1% of low viscosity carboxymethyl cellulose (Sigma). Acetylated glucuronoxylan was recovered from birch wood flakes by hot water extraction. β-Xylosidase was assayed as described by Bachmann and McCarthy, *J. Gen. Microbiol.*, 135:293–299 (1989) using 5 mM p-nitrophenyl-β-D-xylopyranoside in 50 mM potassium phosphate buffer at pH 7.0. The values of the Michaelis constant ($K_m$) and the maximum velocity ($V_{max}$) were determined from a Lineweaver-Burke plot of assayed activities over a range of substrate concentrations. Suitably diluted xylanases were incubated with alkali-soluble birch wood or oat spelt xylan at concentrations ranging from 0.5 to 10 mg/ml under the assay conditions given.

Xylanase activity was measured at pH values from 4 to 10 under standard assay conditions using oat spelt xylan as a substrate. Buffers used were 100 mM sodium acetate (pH 4 to 4.4); 100 mM potassium phosphate (pH 6 to 8); 100 mM glycine-NaOH (pH 9 to 10). Enzyme activities were also assayed at temperatures from 30° to 70° C. at pH 7.0.

Thermal stability was studied by incubating each purified enzyme (0.5 IU) at 60° C. in 100 mM potassium phosphate buffer at pH 7.0 in the absence of substrate. Aliquots were removed at different times between 0 and 3 hours and were immediately cooled on ice. Residual activity at 70° C. was assayed under standard conditions. Residual enzymatic activity was determined after incubating the purified enzymes in 50 mM phosphate buffer at pH 7.0.

The isoelectric point was determined by isoelectric focusing performed on a Bromma 2117 Multiphor™ horizontal slab-gel system (LKB) using Servalyt Precotes™ (pH 3–10, Serva, Germany). The physicochemical characteristics are summarized in Table 9.

Protein purity and molecular weight of the purified isoenzymes of B-12-2 were determined by SDS-PAGE on a Pharmacia Phast System using 10%–15% gradient polyacrylamide gels using BioRad low molecular weight standards (14,400–97,400 MW). Staining was with Coomassie Brilliant Blue G250.

Temperature and pH optima were determined as previously described (Grabski and Jeffries, 1991).

Table 9 demonstrates that xylanases 1a and 1b (xyl 1a and 1b, group 1) were low molecular weight enzymes with neutral and basic isoelectric points (pI), respectively. Xylanases 2, 3, and 4 (xyl 2, 3, and 4, group 2) had higher molecular weights and acid pIs. These latter enzymes retained greater activity at higher temperatures and greater activity in the alkaline region than did xyl 1a and 1b, even though the latter enzymes had similar temperature and pH optima. Xyl 2, 3, and 4 retained about 40% of their original activity after 3 hours at 60° C. (pH 7.0) while xyl 1a and 1b were almost completely inactivated after 1 hour of incubation.

Group 1 enzymes are not glycosylated. The group 2 enzymes appear to be glycosylated to different extents. Xylanase 2 is apparently strongly glycosylated while 3 and 4 are only weakly glycosylated.

TABLE 9

Chemical and physical properties of xylanase isoenzymes purified from Streptomyces B-12-2

| PARAMETER | xyl 1a | xyl 1b | xyl 2 | xyl 3 | xyl 4 |
|---|---|---|---|---|---|
| Temperature opt. | 55° C. | 60° C. | 60° C. | 60° C. | 60° C. |
| Residual activity at 70° C. | 16% | 7% | 46% | 48% | 34% |
| Residual activity after 2 hr at 60° C. | 15% | 18% | 76% | 72% | 13% |
| Relative molecular weight ($mw_r$) | 26.4 | 23.8 | 36.2 | 36.2 | 40.5 |
| Isoelectric point | 7.5 | 8.3 | 5.4 | 5.0 | 4.8 |
| pH optimum | 6.0 | 6.0 | 7.0 | 7.0 | 6.0 |
| Residual activity | | | | | |
| pH 8.0 | 13% | 15% | 34% | 45% | 22% |
| pH 9.0 | 8% | 10% | 32% | 43% | 1% | b. Chromophore Release

The substantially purified xylanase isoenzymes obtained from B-12-2 were diluted and applied to softwood kraft pulp in a similar manner to the chromophore release assay described above for the crude enzyme preparations. In general, the treated pulp was incubated with the enzyme, washed, extracted with NaOH, and bleached with an amount of bleach determined from the kappa of the enzyme-treated pulp.

Samples (10 g) of kraft pulp were incubated for 3 hours with 5 IU/g pulp of purified xylanase fractions xyl 1, 2, 3 and 4. These experiments were performed before xyl 1a and 1b were resolved from xyl 1. The pulps were then extracted with 1% NaOH (w/w) at 65° C. for 1 hr as previously described. Chromophores released from the pulps immediately following enzyme treatment (Stage 1) and following alkali extraction (Stage 2) were measured at 237 and 465 nm. As is shown in Table 10, Each of the four xylanase fractions was able to release chromophores from softwood kraft pulp. Fraction xyl 2 was the most effective in Stage 1 and fraction xyl 3 was most effective in Stage 2.

TABLE 10

Chromophore release from softwood kraft pulp by B-12-2 xylanases

| | Stage 1 | | Stage 2 | |
| --- | --- | --- | --- | --- |
| | 237 nm | 465 nm | 237 nm | 465 nm |
| Control | 7.3 | 0.7 | 37.2 | 3.2 |
| xyl 1 | 20.5 | 1.2 | 60.6 | 4.0 |
| xyl 2 | 22.8 | 1.1 | 76.0 | 4.4 |
| xyl 3 | 18.2 | 1.1 | 86.6 | 5.0 |
| xyl 4 | 10.0 | 0.9 | 66.4 | 4.3 |

Each of the five substantially purified xylanase isoenzymes from B-12-2 obtained by purification on the hydrophobic interaction column were also tested for capacity to release chromophores from a hardwood (red oak) kraft pulp as follows. Conditions were the same as above. As is shown in Table 11, when all enzyme preparations were applied at an equal level (5 IU/g pulp, as determined by activity assays), the crude enzyme mixture was most effective at releasing chromophores. Of the various purified enzyme fractions, xyl 1a was the most effective.

TABLE 11

Chromophore release from hardwood kraft pulp by B-12-2 xylanases

| Xylanases | Abs at 237 nm per gram oven dry pulp |
| --- | --- |
| control (boiled crude) | 12.8 |
| crude | 79.2 |
| xylanase 1a | 48.2 |
| xylanase 1b | 39.8 |
| xylanase 2 | 44.4 |
| xylanase 3 | 39.6 |
| xylanase 4 | 37.4 | c. Enzyme-enhanced bleaching of hardwood pulp by purified xylanases from Streptomyces sp. TUB B-12-2. A commercial, oven-dried (OD) hardwood kraft pulp (kappa number=10, consistency=10%) was bleached, either with or without pre-treatment using purified Streptomyces sp. TUB B-12-2 xylanases. In each experimental sample, 20 g of OD pulp was treated with a total of 3 IU/g of xylanase at 60° C. for three hours in a 50 mM potassium phosphate buffer at pH 7.0.

The pre-treated and control pulps were vacuum-filtered and were washed several times with distilled water before chromophore release and sugar release were measured. Table 12 reports the chromophore release ($A_{237}$ per gram of oven dried pulp) and the total sugar and reducing sugar profile per gram of oven dried pulp. Chromophore release was markedly enhanced by either xylanase alone and was enhanced even more when a combination of the two was tested. Both the total sugar and reducing sugar were greater after xylanase treatment. Xyl 3 appears to have higher activity than xyl 1a in both the chromophore and sugar release assays.

TABLE 12

| Enzyme Added | $A_{237}$ | Reducing Sugars (mg) | Total Sugars (mg) |
| --- | --- | --- | --- |
| No Enzyme | 14.7 | 0.000 | 2.9 |
| xyl 1a | 66.4 | 2.6 | 17.9 |

TABLE 12-continued

| Enzyme Added | $A_{237}$ | Reducing Sugars (mg) | Total Sugars (mg) |
| --- | --- | --- | --- |
| xyl 3 | 87.4 | 6.6 | 19.5 |
| xyl 1a + xyl 3[a] | 97.3 | 6.8 | 24.2 |

[a]1.5 IU of each enzyme was added per gram of pulp

The effect of enzyme dose on chromophore release and sugar release from a commercial hardwood pulp was measured as follows. Samples of 1 g of the oven dried pulp (kappa number=10, consistency=10%) were treated at 60° C. for three hours in a 50 mM potassium phosphate buffer at pH 7 in the presence of increasing amounts of either xyl 1a or xyl 3 in the range of 0.5 to 5 IU/g of pulp. Both enzyme preparations released similar amounts of chromophore over an enzyme dose range of about 1 to 5 IU/g, with the chromophore release ($A_{237}$) increasing generally linearly with increasing enzyme dose. Chromophore release by xyl 1a increased from 56 units at 0.5 IU of enzyme per gram to 85 units at 5 IU per gram. When xyl 3 was tested, chromophore release over the same enzyme dosage range increased from 45 units to 93 units. Xyl 3 showed less of a plateau than xyl 1 at higher doses and its chromophore release was proportional to enzyme dose over a wider range. Although both enzymes released approximately the same amount of total sugars (12–24 mg/g dry pulp) over the tested enzyme dosage range, xyl 3 clearly released more reducing sugars from pulp than did xyl 1a. Xyl 1a released 2–4 mg of reducing sugars per gram over the tested range while xyl 3 released continuously increasing amounts of reducing sugars with increased enzyme dose. Xyl 3 released 2–8 mg of reducing sugars, with a generally linear increase observed over the entire dosage range. Thus, xyl 3 exhibited relatively more activity than xyl 1 against kraft pulp even though the two had similar activities against pure xylan.

Following enzyme treatment, each experimental sample and control sample was taken through a bleaching sequence. The conditions of each bleaching step are shown in Table 13. $C_{70}/D_{30}$ refers to a 70:30 mixture of $Cl_2$ and $ClO_2$. E refers to alkaline extraction with 1% NaOH. The $D_1$ stage refers to treatment with $ClO_2$ alone. Pulp brightness was measured after two different bleaching stages. The brightness of the enzyme-pretreated samples and the control are shown in Table 14.

TABLE 13

| Bleaching Stage | Consistency (%) | Temperature (°C.) | Time (Min) | Active Chlorine Charge (%) | NaOH (%) |
| --- | --- | --- | --- | --- | --- |
| $C_{70}/D_{30}$ | 3.5 | 45 | 30 | 1.62 | 0.0 |
| $E_1$ | 12 | 65 | 90 | 0.0 | 1.0 |
| $D_1$ | 12 | 65 | 180 | 0.5 | 0.0 |

TABLE 14

| | Brightness | |
| --- | --- | --- |
| Enzyme Added | $C_{70}/D_{30}$-$E_1$ | $D_1$ |
| No enzyme | 46.4 | 62.8 |
| xyl 1a | 51.9 | 68.6 |
| xyl 3 | 52.4 | 71.3 |
| xyl 1a + xyl 3[a] | 54.6 | 73.0 |

[a]1.5 IU of each enzyme was added per gram of pulp

These data demonstrate that enzyme pre-treatment with xyl 1a, xyl 3, or a mixture of xyl 1a and xyl 3 from Streptomyces sp. TUB B-12-2 increases the brightness of subsequently bleached hardwood pulp when compared to untreated pulp. Treatment with xyl 3 results in greater brightness increases than treatment with xyl 1a. An apparent synergism was observed between xyl 1a and xyl 3 when the two were mixed equally. The relative ratios of the two purified enzymes was not optimized for maximal brightness in these experiments. Thus, it is possible that other effects on brightness would be observed at different xyl 1a:xyl 3 ratios.

d. Hydrolysis studies. The extent of hydrolysis of acetylglucuronoxylan, arabinoxylan and birch xylan (Sigma) by the d. Hydrolysis studies. The extent of hydrolysis of acetylglucuronoxylan, arabinoxylan and birch xylan (Sigma) by the purified B-12-2 xylanases was evaluated by measuring the release of reducing sugars (NS) from 0.25% substrate solutions in 50 mM pH 7.0 phosphate buffer at 40° C. in the presence of 0.1 IU of purified enzyme in a final volume of 1.0 ml. Time-course experiments were terminated when an increase in reducing sugars was no longer detected. Hydrolyses of aryl-$\beta$-D-cellobioside) were performed at 50° C. using 0.1 IU of purified enzyme and 5 MM substrate in 1.0 ml of above buffer. The release of PNP group was determined spectrophotometrically at 400 nm. Synergism among purified xylanases was determined using alkali soluble oat spelt xylan (1% w/v) or washed, unbleached kraft pulp from southern red oak (Quercus falcata) (10% w/v). In the case of soluble oat spelt xylan, hydrolyses were carried out for 24 hours at 40° C.; in the case of the pulp, hydrolyses were carried out for 3 hours at 60° C. Turbidity-clearing assays were performed at 50° C. using 0.5 IU of each enzyme preparation (as determined by NS) plus 2 mg of water insoluble xylan in a final volume of 1.0 ml of 50 mM phosphate buffer, pH 7.0. Turbidities (620 nm) were read directly up to 4 h.

Acidic endoxylanases achieved a higher degree of hydrolysis as compared to basic endoxylanases when acting on acetylglucuronoxylan, oat spelt arabinoxylan or birch glucuronoxylan (Table 12). Among the acidic endoxylanases no significant differences were found in their extents of hydrolysis. In contrast, basic endoxylanases showed different capacities to hydrolyze acetylxylan. In fact, xyl 1a could release almost as much reducing sugars from this substrate as could the acidic endoxylanases.

TABLE 15

Extent of hydrolysis of various xylans[a]

| Substrate | Enzyme | | | | |
|---|---|---|---|---|---|
| | xyl 1a | xyl 1b | xyl 2 | xyl 3 | xyl 4 |
| Acetylglucuronoxylan | 5.4 | 3.8 | 6.8 | 7.0 | 6.7 |
| Oat spelt | 12.0 | 13.7 | 19.8 | 19.2 | 20.7 |
| Birchwood | 16.0 | 16.9 | 24.2 | 24.3 | 26.5 |

[a] all values in % of initial substrate

The cooperative activity among the different endoxylanases was investigated using both oat spelt arabinoxylan and a more complex substrate (unbleached red oak pulp). Using substrate limiting conditions no synergism was detected among endoxylanases in the degradation of the oat spelt arabinoxylan. Sugar release was additive and did not exceed the amount observed with group 2 (xyl 2, 3 and 4) enzymes. In contrast, experiments carried out using unbleached red oak pulp showed that the isoenzymes have different capacities to release sugars from this substrate (data not shown). Total sugars released from pulp by a combination of xyl 1b and xyl 3 resulted in 20 to 30% increase in sugars production (as measured by the phenol-sulfuric acid method), beyond what could be obtained with either enzyme individually, demonstrating that synergism exists between these two enzymes. The ratio between total sugars (as determined by the phenol-sulfuric method) and reducing sugars (as measured by NS) revealed that group 1 (xyl 1a and xyl 1b) tend to produce larger xylo-oligosaccharides. When a mixture of xyl 1a plus xyl 3 or xyl 1b plus xyl 3 was used, the ratio of total sugars/reducing sugars decreased, to the value obtained with only xyl 3 even though the total sugars released was greater. This fact suggests that xylo-oligosaccharides produced by xyl 1a and xyl 1b can be further degraded by xyl 3.

e. Substrate affinities. The kinetic parameters were determined using both arabinoxylan (oat spelt) and a lesser-substituted glucuronoxylan (birch wood xylan) as substrates. All isoenzymes were more active on the birch xylan (Table 13). We observed substrate inhibition at higher xylan concentrations (>2.5 mg/ml)—especially with the acidic endoxylanases—when we plotted the data by the method of Lineweaver-Burke. The kinetic parameters were therefore obtained by extrapolating from the linear region.

TABLE 16

Kinetic properties of endoxylanases from Streptomyces sp. B-12-2

| Substrate | Enzyme Property | | | | |
|---|---|---|---|---|---|
| | xyl 1a | xyl 1b | xyl 2 | xyl 3 | xyl 4 |
| Oat spelt xylan | | | | | |
| Sp. activity (mmol min$^{-1}$ mg$^{-1}$) | 97.4 | 216.0 | 138.3 | 283.4 | 224.8 |
| $K_m$ (mg/ml) | 5.8 | 3.4 | 3.0 | 1.2 | 0.8 |
| Vmax (units mg$^{-1}$) | 162.5 | 470.7 | 210.0 | 338.0 | 243.0 |
| $K_{cat}$ (sec$^{-1}$) | 71.5 | 162.9 | 126.7 | 203.9 | 164.0 |
| Birchwood xylan | | | | | |
| Sp. activity (mmol min$^{-1}$ mg$^{-1}$) | 105.2 | 285.2 | 117.5 | 268.3 | 242.7 |
| $K_m$ (mg/ml) | 3.4 | 2.7 | 1.1 | 0.8 | 0.5 |
| $V_{max}$ (units mg$^{-1}$) | 141.8 | 410.8 | 169.0 | 368.2 | 279.1 |
| $K_{cat}$ (sec$^{-1}$) | 62.4 | 186.7 | 101.9 | 222.0 | 184.9 | f. Action pattern studies. The hydrolysis of xylans was performed as previously reported by Patel et al., *Appl. Microbiol. Biotechnol.*, 39:405–412 (1993) using soluble and insoluble xylan from oat spelt and birchwood. Hydrolysis products of xylo-oligosaccharides were determined by incubating 0.05 IU of purified endoxylanases with 1 mg of xylobiose ($X_2$), xylotriose ($X_3$), xylotetraose ($X_4$) or xylopentaose ($X_5$) (Megazyme, North Rocks, Australia) in 1.0 ml of 50 mM phosphate buffer, pH 7.0 overnight at 50° C. Enzymes were inactivated by boiling for 10 min. Hydrolysates were analyzed by HPLC using a CARBOPAC PA1™ column equipped with a pulsed amperometric detector (Dionex). The standard mixture contained 20 mM of each xylo-oligosaccharide ($X_2$ to $X_5$), xylose, and L-arabinose.

Figure 21:
FIGS. 21–23 depict the profile of hydrolysis products obtained on various substrates using individual xylanase enzymes purified from strain B-12-2.
Figure 22:
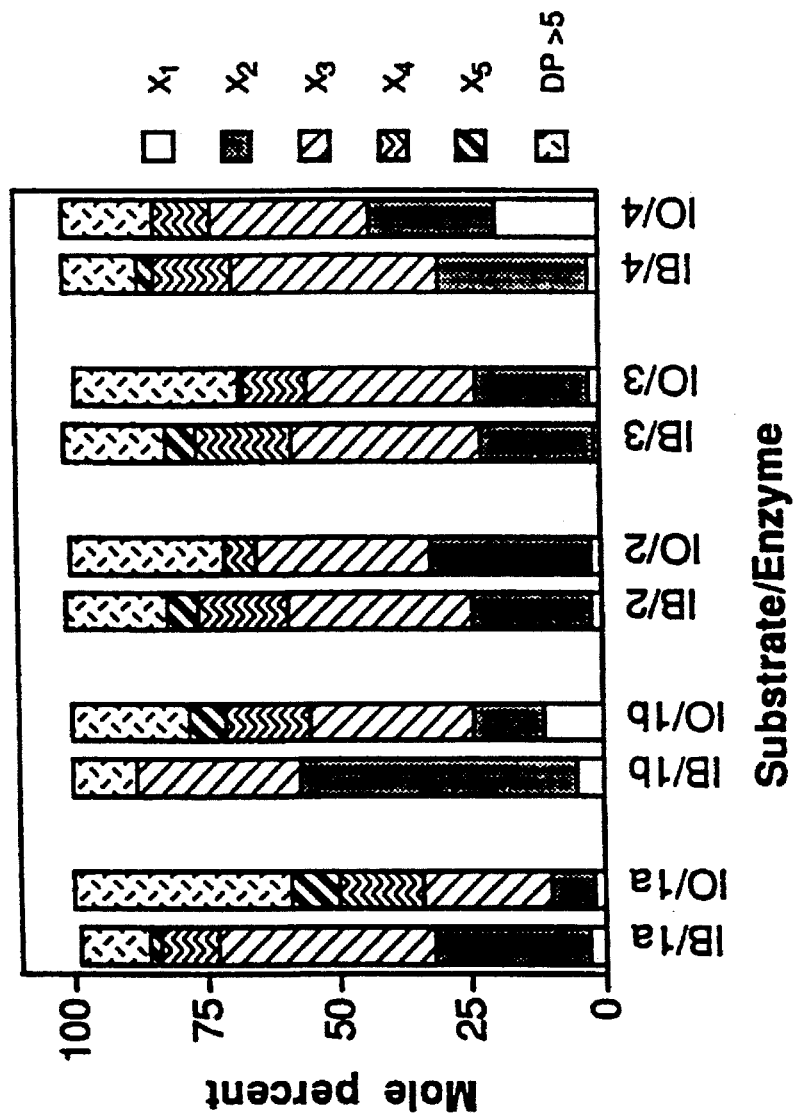

The action patterns of each of the purified enzymes using water soluble and water insoluble oat spelt arabinoxylan and birch xylan are reported in FIGS. 21 and 22. The experimental conditions used were selected to minimize the extent of hydrolysis and thus to enable the identification of any intermediates. Although none of the enzymes tested were able to release arabinose, remarkable differences were noted in using different substrates. The hydrolysis of both soluble and insoluble oat spelt arabinoxylan resulted in larger amounts of xylo-oligosaccharides with DP>5, and $X_3$ was the main product regardless of the enzyme used. Xylobiose ($X_2$) was the major product following hydrolysis of soluble birchwood xylan for all enzymes except xyl 1a.

Xyl 1a showed only limited action on soluble or insoluble oat arabinoxylan. In contrast, xyl 1b appeared to be the most active enzyme on soluble or insoluble birch xylan. In the case of insoluble birchwood xylan, most enzymes formed $X_3$ as the major hydrolysis product along with $X_4$ and $X_5$ with the exception of xyl 1b that produced mostly $X_2$ and no $X_5$ from the soluble and insoluble birch substrate. Xylose was only a small percentage of the total but was present as a product of all enzymes when they were acting on polymeric substrate.

Figure 23:
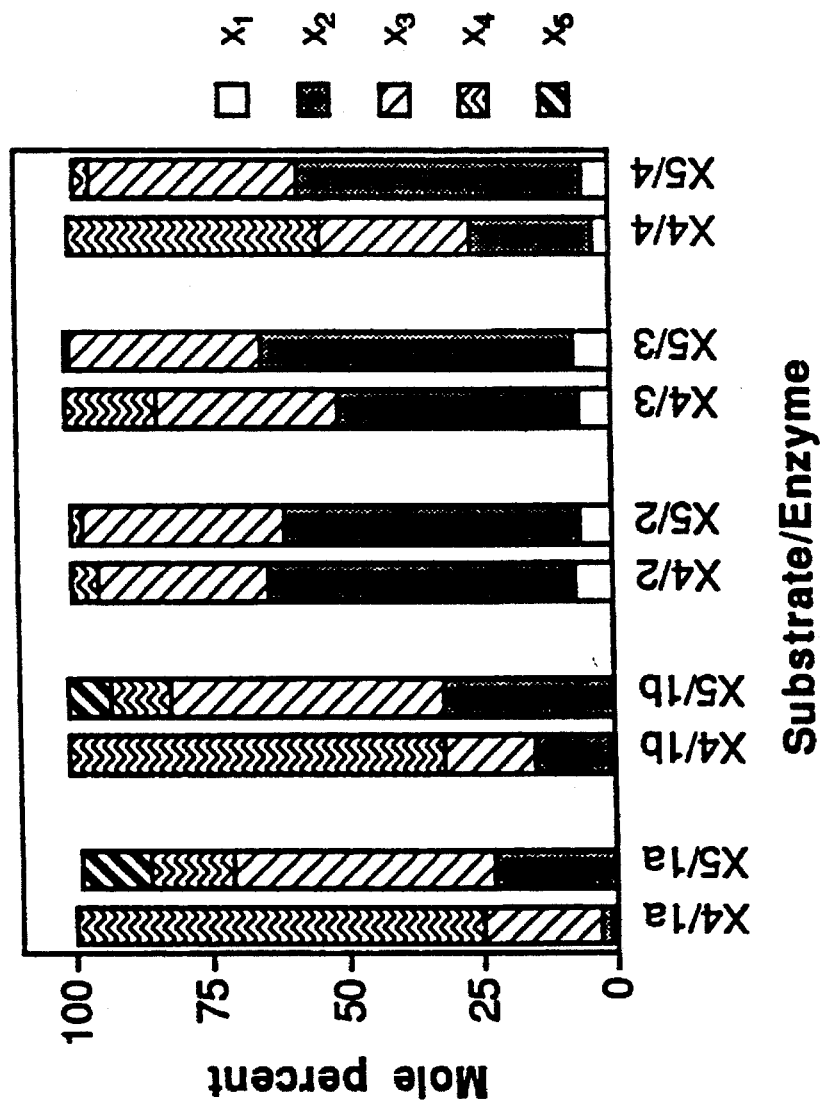

The action patterns of the endoxylanases were further investigated using purified xylo-oligosaccharides as substrate. None of the endoxylanases showed activity on $X_2$ or $X_3$. They were able to cleave $X_4$ and $X_5$ but to different extents. FIG. 23 shows the molar percentage of the products obtained from the hydrolysis of the xylo-oligosaccharide substrates. Acidic (group 2) endoxylanases completely hydrolyzed $X_5$ producing mostly $X_3$ and $X_2$, but also $X_4$ and small amounts of xylose. The hydrolysis of $X_4$ and $X_5$ by basic (group 1) endoxylanases was much slower and xylose was not formed in the conditions used. The production of $X_4$ without the formation of xylose from $X_5$ and the disproportionately small amount of $X_2$ present in the hydrolysate of $X_5$ suggested that the basic enzymes, xyl 1a and 1b carry out transglycosylation to produce $X_4$ from $X_2$.

f. Effectors. We investigated the effects of 1 mM metal ions and other agents on the activities of purified endoxylanases (Table 14). The isoenzymes were not significantly influenced by $Ca^{2+}$ and $Mg^{2+}$ but were totally inactivated by $Hg^{2+}$ and N-bromosuccinamide. Other compounds such as EDTA, SDS and $Cu^{2+}$ and $Fe^{2+}$ showed only partial inhibition depending on the enzymes. p-Hydroxymercury-benzoate (PHMB), affected only xylanase 1b, which was completely inactivated. The different inhibitions by $HgCl_2$ and PHMB suggests the presence of a relatively hydrophobic pocket at the catalytic site of xyl 1b. Phenylmethylsulfonylfluoride (PMSF), a classical inhibitor of serine-proteases did not influence the activity of any enzyme, indicating that serine residues are not involved in the active site. The total inactivation due to $Hg^{2+}$ and N-bromosuccinamide has already been reported for xylanases of different origins and could be due to the presence of a tryptophan residue probably conserved among xylanases.

TABLE 17

Effect of various reagents on the activity of purified endoxylanases

| Reagent | Relative activity (%) | | | | |
|---|---|---|---|---|---|
| | xyl 1a | xyl 1b | xyl 2 | xyl 3 | xyl 4 |
| $CaCl_2$ | 108 | 100 | 100 | 100 | 104 |
| $MgCl_2$ | 100 | 100 | 100 | 100 | 100 |
| $CuCl_2$ | 90 | 85 | 59 | 72 | 74 |
| $FeSO_4$ | 100 | 100 | 100 | 71 | 89 |
| $HgCl_2$ | 0 | 0 | 0 | 0 | 0 |
| EDTA | 80 | 82 | 100 | 100 | 100 |
| SDS | 89 | 100 | 100 | 89 | 89 |
| PHMB | 100 | 0 | 90 | 96 | 95 |
| PMSF | 95 | 87 | 100 | 100 | 100 |
| N-Bromosuccinamide | 0 | 0 | 0 | 0 | 0 | h. Summary of B-12-2 xylanase characteristics. The DNS assay is often used in screening for xylanase activities because it is rapid, easy to use, and sensitive. This latter feature however, can also lead to misinterpretation because depending on the enzyme and the extent of hydrolysis, the DNS assay gives a 3 to 10-fold higher value for xylanase activity than does the NS assay. In the present work, we found about 4- to 5-fold higher activity units by DNS than by NS in assaying crude activity for B-12-2. We believe that the higher value obtained with DNS results from partial degradation of the xylan as in the case in the analysis of cellodextrins.

Analysis of the purified proteins by SDS/PAGE and isoelectric focusing indicated that the endoxylanases produced by Streptomyces B-12-2 are classified as low $M_r$/basic (group 1) and high $M_r$/acidic (group 2) xylanases (Table 9). None of the purified isoenzymes was able to release arabinose from oat spelt xylan. This is consistent with a higher affinity (lower $K_m$) for less branched (birchwood glucuronoxylan) than for the highly substituted oat spelts arabinoxylan (Table 13). Nevertheless, the specific activity and $V_{max}$ were in some cases higher using oat spelt xylan as the substrate. This could result from higher solubility or reactivity of oat spelt arabinoxylan, and it indicates that a substituted substrate may be required for maximal activity in some cases. It is noteworthy in this respect that arabinoxylans (oat spelt and corn stalk) were the best inducers for overall xylanase activity. In general, group 2 enzymes showed higher affinities than group 1 enzymes, regardless of the substrate.

The xylanases isolated from Streptomyces B-12-2 are all endo-acting enzymes as demonstrated by their hydrolysis products (FIGS. 21-23). However, the type of substrate used clearly influences their action patterns and the ratios of the main products. The greater amount of higher DP xylo-oligosaccharides obtained from oat spelt xylan hydrolysis as compared to birchwood is probably due to the higher degree of branching of the former substrate.

The results obtained from the hydrolysis of the $X_4$ and $X_5$ substrates allowed a clear classification of the group 1 and group 2 enzymes based on their action patterns. We discerned differences in the ratios among the products with polymeric substrates, but quantitative analysis was possible only up to DP 5. The group 1 endoxylanases (xyl 1a and xyl 1b) appear to have a "more endo" action pattern in that they did not degrade $X_4$ to a significant extent and they did not fully hydrolyze $X_5$. The group 2 endoxylanases (xyl 2, 3, 4)

degraded $X_4$ to various extents and completely hydrolyzed $X_5$ indicating that they are able to act on lower DP substrates. Moreover, the mode of action of the group 2 endoxylanases seemed to be different in that they formed small amounts of xylose. This is probably due to a lower specificity in the bond-cleavage of the acidic, group 2 proteins. The acidic, group 2 endoxylanases in the present study produced a higher degree of hydrolysis with all tested xylans (Table 12).

The group 1 enzymes could be clearly distinguished from group 2, by their different action patterns on $X_4$ and $X_5$. In general, group 2 enzymes—having low pI, high $M_r$, and lower $K_m$ —formed lower DP products from $X_4$ and $X_5$ (FIG. 23). When hydrolyzing birchwood glucuronoxylan, the action patterns of group 2 enzymes were not clearly distinguishable from group 1.

Xyl 1b showed the highest specific activity ($V_{max}$) against both birch and oat spelt substrates, but xyl 3 showed the highest turnover number. When activities were normalized based on production of reducing groups as determined by the NS assay, xyl 1b produced the most $X_2$ from birch xylan; it was the most active in the turbidity clearing assay. Xyl 1b generally exhibited the most endo action pattern by producing higher oligo DP products—especially on insoluble substrates. It had the highest $V_{max}$ and the second highest $K_m$.

Within group 1, xyl 1a and xyl 1b clearly differed. Xyl 1b was inactivated by PHMB, and the catalytic turnover rate of xyl 1b was approximately two to three times higher than xyl 1a. These findings suggest that xyl 1a and xyl 1b could represent different classes of endoxylanses. We noted that group 1 enzymes formed $X_4$ from $X_5$ without the apparent production of xylose. This, plus the elevated ratios of $X_3$ to $X_2$ when the enzymes acted on $X_5$, suggest that group 1 enzymes produced $X_4$ by transglycosylation of $X_2$. Group 2 enzymes did not exhibit transglycosylation by this measure.

The acidic, group 2 xylanases (xyl 2, 3 and 4) were remarkably similar in most physicochemical and kinetic characteristics. Xyl 2 could be distinguished by its high degree of glycosylation (FIG. 3), its lower $V_{max}$ value on oat spelt or birch xylan and its greater ability to degrade $X_4$.

The xylanase isoenzymes from *S. roseiscleroticus* were classified as endo-1 and endo-2 depending on their hydrolysis products from oat spelts arabinoxylan. Endo-1 xylanases tended to hydrolyze the arabinoxylan more completely while endo-2 produced a greater amount of larger oligosaccharides. Our current results seem to partially confirm the previous data. However, use of birch glucuronoxylan in place of oat spelts arabinoxylan leads to a very different pattern with respect to unhydrolyzed substrate. The endo-1 character could be attributed to a greater ability to bind shorter oligosaccharides and its ability to perform their hydrolysis. The different affinities in binding could be specially important in the degradation of complex substrates. Indeed, with increased substrate complexity, the accessibility of some moieties could be limited to xylanases having a smaller catalytic active site. In this respect we found a synergistic action between acidic endoxylanases and basic endoxylanases only when a complex substrate was used (unbleached red oak pulp).

There are very few reports dealing with the complete characterization of xylanase isoenzymes produced by a single organism. *S. lividans* is probably the best characterized streptomycete in this respect. The results reported therein confirm the greater catalytic versatility, of the high-molecular-mass endoxylanases versus the low-molecular-mass-endoxylanases within the limits of the substrates tested here. The action patterns and catalytic properties are similar within the group 2 enzymes. This suggests that their multiplicities may be due to other properties. Only one acidic enzyme (xln A) is produced by *S. lividans*, and it appears to have somewhat different properties than the three acidic xylanases reported here. In contrast to *S. lividans*, none of the Streptomyces B-12-2 acidic endoxylanases is able to cleave $X_3$ or PNP-xyloside. The shortest xylo-oligosaccharides hydrolyzed by both low-molecular-mass-basic and high-molecular-mass-acid endoxylanases from B-12-2 are $X_4$ and $X_5$. The acidic endoxylanases from Streptomyces B-12-2 are glycosylated. Xyl 2 was the most glycosylated of the Streptomyces sp. B-12-2 xylanases; xyl 3 was the most thermal and alkali stable and it was recovered in the highest yield, it was not heavily glycosylated.

We claim:

1. A method of removing color from wood pulp comprising the steps of:
   (a) preparing a wood pulp;
   (b) treating the wood pulp with xylanase wherein the xylanase is capable of releasing chromophores from the pulp; and
   (c) extracting the wood pulp to remove chromophores said xylanase being isolated xyl 3 obtained from *Streptomyces roseiscleroticus* NRRL B-11019, wherein xyl 3 has a molecular weight of approximately 21 kD as determined by SDS-gel electrophoresis and a pH optima of pH 5.0—7.0.

2. The method of claim 1 wherein the wood pulp is a kraft pulp.

3. The method of claim 2 wherein the kraft pulp is a softwood pulp.

4. The method of claim 2 wherein the kraft pulp is a hardwood pulp.

5. The method of claim 1 wherein the extracting is with an alkali solution.

6. The method of claim 1 wherein the extracting is with an alkali and hydrogen peroxide solution.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Streptomyces roseiscleroticus
        ( B ) STRAIN: NRRLB-11019

( x i ) SEQUENCE DESCRIPTION: SEQ ID NO:1:

Ala Glu Ser Thr Leu Gly Ala Ala Ala Ala Gln Ser Gly Arg Tyr Phe

```
                1                5                          10                          15
             Gly  Thr  Ala  Ile  Ala  Ala  Gly  Arg  Leu  Gly
                                 20                   25
```

( 2 ) INFORMATION FOR SEQ ID NO:2:

( i ) SEQUENCE CHARACTERISTICS:
    ( A ) LENGTH: 29 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Streptomyces roseiscleroticus
    ( B ) STRAIN: NRRLB-11019

( x i ) SEQUENCE DESCRIPTION: SEQ ID NO:2:

```
    Xaa  Thr  Val  Val  Thr  Thr  Asn  Gln  Thr  Gly  Thr  His  Glu  Gly  Tyr  Tyr
    1                 5                              10                          15

Tyr  Ser  Phe  Xaa  Thr  Asp  Ala  Pro  Asn  Asp  Ser  Thr  Tyr
                   20                      25
```

( 2 ) INFORMATION FOR SEQ ID NO:3:

( i ) SEQUENCE CHARACTERISTICS:
    ( A ) LENGTH: 33 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Streptomyces roseiscleroticus
    ( B ) STRAIN: NRRLB-11019

( x i ) SEQUENCE DESCRIPTION: SEQ ID NO:3:

```
    Ala  Thr  Thr  Ile  Thr  Thr  Asn  Gln  Thr  Gly  Tyr  Asp  Gly  Met  Tyr  Tyr
    1                 5                              10                          15

Ser  Phe  Trp  Thr  Asp  Gly  Xaa  Xaa  Ser  Val  Xaa  Met  Thr  Leu  Asn  Xaa
                   20                      25                          30

Gly
```

( 2 ) INFORMATION FOR SEQ ID NO:4:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:

(A) ORGANISM: Streptomyces roseiscleroticus
(B) STRAIN: NRRLB-11019

(xi) SEQUENCE DESCRIPTION: SEQ ID NO:4:

```
Ala Glu Ser Thr Leu Gly Ala Ala Ala Gln Gln Ser Gly Tyr Tyr Phe
 1           5                   10                  15
Gly Thr Ala Ile Ala Ala Gly Leu Leu
            20                  25
```